United States Patent [19]

Fabre et al.

[11] Patent Number: 4,539,400

[45] Date of Patent: Sep. 3, 1985

[54] PYRIDIN-3-YL SUBSTITUTED ORTHO-FUSED PYRROLE DERIVATIVES

[75] Inventors: Jean-Louis Fabre, Paris; Daniel Farge, Thiais; Claude James; Daniel Lavé, both of Paris, all of France

[73] Assignee: Rhone-Poulenc Sante, Courbevoie, France

[21] Appl. No.: 569,909

[22] Filed: Jan. 11, 1984

[30] Foreign Application Priority Data

Jan. 13, 1983 [FR] France ................................ 83 00453
Jan. 13, 1983 [FR] France ................................ 83 00454

[51] Int. Cl.³ ................. C07D 471/04; C07D 487/04; C07D 498/04; C07D 513/04
[52] U.S. Cl. ..................................... 544/47; 546/272; 548/453
[58] Field of Search .......................... 546/272; 544/47; 548/453

[56] References Cited

U.S. PATENT DOCUMENTS 3,544,590 12/1970 Kittleson ............................. 548/453
3,865,839 2/1975 Allen et al. ......................... 548/453

OTHER PUBLICATIONS

Percy et al., C.A., vol. 75, 1971, 75: 96775d, p. 174.

Primary Examiner—Henry R. Jiles
Assistant Examiner—J. G. Mullins
Attorney, Agent, or Firm—Stevens, Davis, Miller & Mosher

[57] ABSTRACT

The invention provides new derivatives of the formula:

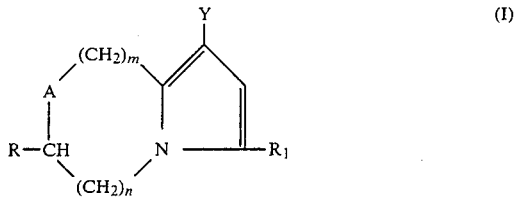

(I)

in which either (a) Y=COOH or a radical of the formula (II), in which $R_2$=alkyl or benzyl, A=a sulphur atom, m=1, n=0, R=pyridin-3-yl and $R_1$=H, or (b) Y=CN, COOH or a radical of the formula

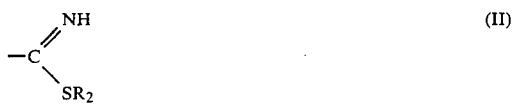

(II)

defined as above, A=S, O or $CH_2$, m=1 or 2 and n=0, 1 or 2, (m+n) being 1, 2 or 3, R=H, alkyl or phenyl (optionally substituted by halogen, alkyl, alkoxy or $CF_3$) and $R_1$=a radical of the formula

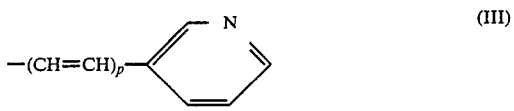

(III)

in which p=0 or 1, the alkyl radicals and alkyl portions being straight-chain or branched-chain and containing 1 to 4 carbon atoms each. Processes for the production of these compounds are described. They are useful as intermediates for the preparation of new medicaments.

14 Claims, No Drawings

PYRIDIN-3-YL SUBSTITUTED ORTHO-FUSED PYRROLE DERIVATIVES

The present invention provides new ortho-fused pyrrole derivatives of the formula:

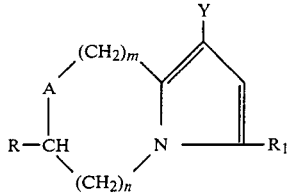
(I)

wherein, either (a) Y represents a carboxyl radical or a radical of the formula:

(II)

in which $R_2$ represents an alkyl or benzyl radical, A represents a sulphur atom, m represents 1, n represents zero, R represents a pyridin-3-yl radical and $R_1$ represents a hydrogen atom, or (b) Y represents a cyano or carboxyl radical or a radical of the formula (II) as defined above, A represents a sulphur or oxygen atom or a methylene radical, m represents 1 or 2 and n represents 0, 1 or 2, the sum of m+n being 1, 2 or 3, R represents a hydrogen atom, an alkyl radical or a phenyl radical (unsubstituted or substituted by a halogen atom or an alkyl, alkoxy or trifluoromethyl radical) and $R_1$ represents a radical of the formula:

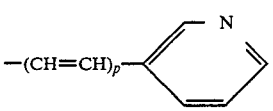
(III)

in which p represents zero or 1, the said alkyl radicals or alkyl portions in the above definitions and in those which follow being straight-chain or branched-chain and, unless mentioned otherwise, containing 1 to 4 carbon atoms.

According to the invention, the compounds of the formula (I) in which Y represents a cyano radical and the other symbols are as defined above under (b), i.e. the compounds of the formula:

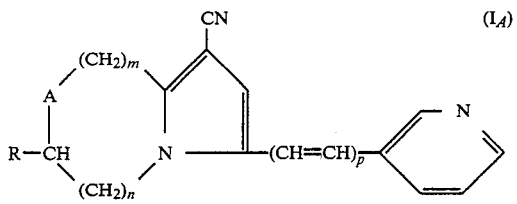
(I$_A$)

are obtained by reacting 2-chloroacrylonitrile of the formula:

(IV)

with a compound of the formula:

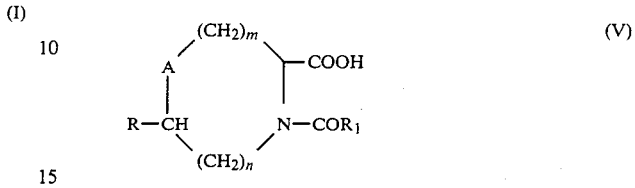
(V)

in which the various symbols are defined as above under (b).

The reaction is generally carried out in acetic anhydride by heating to a temperature of between 80° and 130° C.

The compounds of the formula (V) in which A, R, $R_1$, m and n are as defined above under (b) can be obtained by condensing a compound of the formula:

$$R_1COZ_o \quad (VI)$$

in which $R_1$ is as defined above under (b) and $Z_o$ represents a halogen atom or alternatively forms a mixed anhydride with the radical $R_1CO-$, with a compound of the formula:

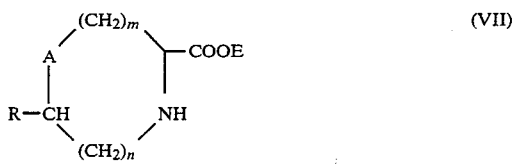
(VII)

in which A, R, m and n are as defined above under (b) and E represents a hydrogen atom or an alkyl radical, followed, where E represents an alkyl radical, by hydrolysis.

The condensation of the compound of the formula (VI) with the compound of the formula (VII) is generally carried out in an inert organic solvent such as chloroform, in the presence of an acid acceptor such as triethylamine, at a temperature of between 0° and 65° C.

In the case where E represents an alkyl radical, the hydrolysis is carried out by any method known to those skilled in the art for converting an ester to an acid without affecting the rest of the molecule, in particular by heating in an alkaline medium, in water or an aqueous-alcoholic solvent such as a water/ethanol mixture, to a temperature of between 20° and 80° C.

The products of the general formula (VII) can be obtained by applying or adapting the methods described by H. T. NAGASAWA, J. A. ELBERLING, P. S. FRASER and N. S. NIZUNO, J. Med. Chem. 14, 501 (1971); B. BELLEAU, J. Med. Chem. 2, 553 (1960); J .C. WRISTON and C. G. McKENzIE, J. Biol. Chem., 225, 607 (1957); S. WOLFF, G. MILITELLO et al., Tet. Letters, 3913 (1979); H. GERSHON and A. SCALA, J. Org. Chem. 26, 2347 (1961); R. RIEMSCHNEIDER and G. A. HOYER, Z. Naturforsch. 17 B, 765 (1962); H. MÖHRLE and C. KARL, Arch. Pharm. 301, 728 (1968); or R. K. HILL, T. H. CHAN and J. A. JOULE, Tetrahedron 21, 147 (1965).

If A represents an oxygen atom, n is equal to 0 and R and m are defined as above under (b), the product of the general formula (VII) is not isolated but the product of the general formula (V) is obtained directly, the condensation of the product of the general formula (VI) taking place in situ in the reaction mixture.

According to the invention, the products of the general formula (I) in which Y represents a carboxyl radical and the other symbols are defined as above, can be obtained by hydrolysing a nitrile of the general formula:

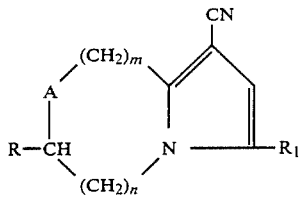
(VIII)

in which the symbols are defined as above, by any method known to those skilled in the art for converting a nitrile to an acid without affecting the rest of the molecule, in particular by heating in an alkaline medium in a high-boiling alcohol such as ethylene glycol, to a temperature of between 100° C. and the reflux temperature of the reaction mixture.

The products of the general formula (VIII) in which the symbols are defined as above under (b), i.e. the products of the general formula ($I_A$), can be prepared as stated above, i.e. by reacting a product of the formula (IV) with a product of the general formula (V).

The products of the general formula (VIII) in which the symbols are defined as above under (a) can be prepared by condensing a product of the formula (IV) with a product of the formula:

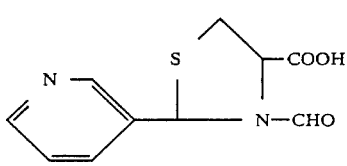
(IX)

The reaction is generally carried out in acetic anhydride by heating to a temperature of between 80° and 130° C.

The product of the general formula (IX) can be prepared by formylating the product of the formula:

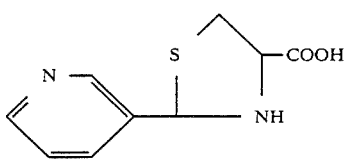
(X)

The formylation can advantageously be carried out by reaction with formic acid in acetic anhydride at a temperature of between 10° and 25° C. The product of the formula (X) can be prepared by the method of A BANASHEK and M. I. SHCHUKINA, J. Gen. Chem. U.S.S.R. 31, 1374 (1961); Chem. Abstr. 55, 24739h (1961).

According to the invention, the products of the general formula (I) in which Y represents a radical of the general formula (II) in which $R_2$ is defined as above and the other symbols are defined as above can be prepared by reacting a halide of the general formula:

$$R_2Z \qquad (XI)$$

in which $R_2$ is defined as above and Z represents a halogen atom, preferably an iodine atom, with a product of the general formula:

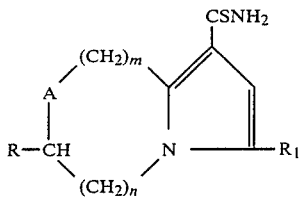
(XII)

in which the symbols are defined as above.

The reaction is generally carried out in an organic solvent such as acetone or a mixture of acetone and dimethylformamide, at a temperature of between 0° and 50° C.

The products of the general formula (XII) can be obtained from a product of the general formula (VIII) by any method known to those skilled in the art for converting a nitrile to a thioamide without affecting the rest of the molecule. It is particularly advantageous to react hydrogen sulphide with the nitrile of the general formula (VIII) in a solvent such as pyridine, in the presence of triethylamine, at a temperature of between 0° and 50° C.

The new products of the general formula (I) can be used, in particular, as intermediates for the preparation of therapeutically active products of the general formula:

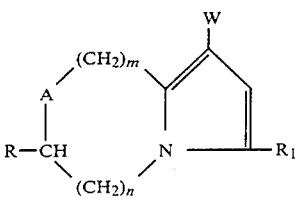
(XIII)

in which either

A—m is equal to 1, n is equal to O, R represents a pyridin-3-yl radical, $R_1$ represents a hydrogen atom and
 (a₁) W represents an acetyl radical, or
 (b₁) W represents a radical of the general formula:

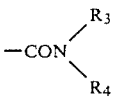
(XIV)

in which:
 $R_3$ represents a hydrogen atom and $R_4$ represents an amino, alkylamino, dialkylamino, phenylamino or dipherylamino radical, or alternatively
 $R_3$ and $R_4$, which are identical or different, represent a hydrogen atom, an alkyl radical containing 1 to 5 carbon atoms or a substituted phenyl radical, or alternatively R$_3$ represents a hydrogen atom and R$_4$ represents a pyridyl radical or an alkyl radical containing 1 to 5 carbon atoms, which is substituted by a carboxyl, amino, alkylamino, dialkylamino, morpholino, piperidino or pyrrolidin-1-yl radical, a piperazin-1-yl radical (optionally substituted in the 4-position by an alkyl radical, pyridyl radical, optionally substituted phenyl radical or optionally substituted benzyl radical), an optionally substituted phenyl radical or a pyridyl or imidazolyl radical, or alternatively R$_3$ and R$_4$ together form an imidazolyl radical or a 5-membered or 6-membered heterocycle which can also contain another heteroatom such as oxygen, sulphur or nitrogen and which is optionally substituted by an alkyl, alkoxycarbonyl, hydroxyalkyl, aminoalkyl, alkylaminoalkyl, dialkylaminoalkyl, pyridyl, pyrimidinyl, pyrazinyl, optionally substituted phenyl or optionally substituted benzyl radical, or (c$_1$) W represents a radical of the general formula:

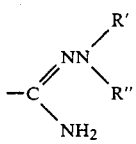 (XV)

in which R' and R'', which are identical or different, represent an alkyl radical, it being understood that, in the above definitions, the substituted phenyl and benzyl radicals are phenyl and benzyl radicals carrying a halogen atom or an alkyl, alkoxy, alkylthio, trifluoromethyl or dialkylamino radical, or alternatively B—m represents the number 1 or 2 and n represents the number 0, 1 or 2, it being understood that the sum of m+n is equal to 1, 2 or 3, A represents a sulphur or oxygen atom or a methylene radical, R represents a hydrogen atom, an alkyl radical or a phenyl radical (optionally substituted by a halogen atom or an alkyl, alkoxy or trifluoromethyl radical), R$_1$ represents a radical of the general formula (III) defined as above and W represents a radical of the general formula:

 (XVI)

in which:

(a$_2$) Q represents an oxygen or sulphur atom or an imino radical and M represents a radical of the general formula:

 (XVII)

in which R$_5$ and R$_6$ both represent a hydrogen atom, or alternatively R$_5$ represents a hydrogen atom and R$_6$ represents a hydroxyl radical or an alkyl radical containing 1 to 5 carbon atoms, which is substituted by a carboxyl, amino, alkylamino, dialkylamino, hydroxyalkylamino, morpholino or imidazolyl radical, a piperazin-1-yl radical [optionally substituted in the 4-position by an alkyl radical, a benzyl radical (optionally substituted by a halogen atom or an alkyl, alkoxy or trifluoromethyl radical) or a phenyl radical (optionally substituted by a halogen atom or an alkyl, alkoxy or trifluoromethyl radical)] or a piperidino or pyrrolidin-1-yl radical, or alternatively R$_6$ represents a phenyl radical substituted by one or more hydroxyl, carboxyl, amino, alkylamino or dialkylamino radicals, or altenatively R$_5$ and R$_6$ form, with the nitrogen atom to which they are bonded, a 5-membered or 6-membered ring which can also contain another heteroatom such as oxygen, sulphur or nitrogen and which is optionally substituted by an alkyl, alkoxycarbonyl, hydroxyalkyl, aminoalkyl, alkylaminoalkyl or dialkylaminoalkyl radical, a benzyl radical (optionally substituted by a halogen atom or an alkyl, alkoxy or trifluoromethyl radical) or a pyrrolidin-1-yl-carbonylalkyl radical, or (b$_2$) Q represents a dialkylhydrazono radical and M represents an amino radical, or (c$_2$) Q and M form a $\delta^2$-thiazolin-2-yl or $\delta^2$-imidazolin-2-yl radical with the carbon atom to which they are bonded.

To obtain the products of the general formula (XIII) defined as above under A in which W represents a radical of the general formula (XIV) in which R$_3$ and R$_4$ together form an imidazolyl ring, N,N'-carbonyldiimidazole is reacted with a product of the general formula (I) in which Y represents a carboxyl radical, R$_1$ represents a hydrogen atom, R represents a pyridin-3-yl radical, m is equal to 1 and n is equal to 0, i.e. a product of the formula:

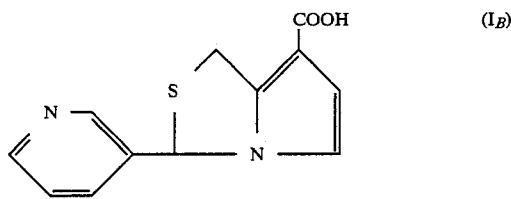 (I$_B$)

The reaction is generally carried out in an inert organic solvent such as tetrahydrofuran or dimethylformamide, at a temperature of the order of 20° C.

To obtain the products of the general formula (XIII) defined as above under A in which W represents a radical of the general formula (XIV) in which R$_3$ and R$_4$ are defined as under (b$_1$), except that R$_3$ and R$_4$ cannot together form an imidazolyl radical, ammonia or an amine of the general formula:

 (XVIII)

in which R$_3$ and R$_4$ have the corresponding definitions, is reacted with a product of the general formula (I) in which Y represents a carboxyl radical, R$_1$ represents a hydrogen atom, R represents a pyridin-3-yl radical, m is equal to 1 and n is equal to 0, i.e. a product of the general formula (I$_B$).

If R$_3$ or R$_4$ represents an alkyl radical containing 1 to 5 carbon atoms, which is substituted by an amino, alkylamino or piperazinyl radical, or alternatively if R$_3$ and R$_4$ together form, with the nitrogen atom to which they are bonded, a 5-membered or 6-membered heterocycle containing another nitrogen atom and optionally substituted by an aminoalkyl radical, the corresponding amine groups must be protected prior to condensation with the acid of the general formula ($I_B$).

The blocking and subsequent unblocking can be carried out by any method known to those skilled in the art for protecting a primary or secondary amine group, e.g. in the form of a trifluoroacetamide, the unblocking being carried out using ammoniacal methanol.

It is particularly advantageous to use the acid of the general formula ($I_B$) in an activated form, e.g.:

($\alpha$) in the form of the acid chloride; in this case, the reaction is carried out in a halogenated solvent such as chloroform, methylene chloride or 1,2-dichloroethane, or an ether such as dioxane, at a temperature of between 20° C. and the reflux temperature of the reaction mixture, or ($\beta$) in the form of a mixed anhydride obtained by reacting an alkyl chloroformate with the acid of the general formula ($I_B$); in this case, the reaction is carried out in a solvent such as ether or tetrahydrofuran or alternatively in dimethylformamide, at a temperature of between 20° and 80° C., or ($\gamma$) in the form of an imidazolide, i.e. a product of the general formula (XIII) in which W represents a radical of the general formula (XIV) in which $R_3$ and $R_4$ together form an imidazolyl radical; in this case, the reaction is carried out in an organic solvent such as tetrahydrofuran or dimethylformamide, or a mixture of these solvents, at a temperature of between 20° and 80° C.

To obtain the products of the general formula (XIII) defined as above under A in which W represents an acetyl radical, the ethoxymagnesium derivative of ethyl malonate is reacted with a halide of the acid of the general formula ($I_B$) defined as above.

The reaction is generally carried out in an organic solvent such as an ether or an alcohol, or a mixture of these solvents, in the presence of an acid acceptor such as triethylamine, at a temperature of between 10° C. and the reflux temperature of the reaction mixture.

To obtain the products of the general formula (XIII) defined as above under A in which W represents a radical of the general formula (XV) defined as above, a hydrazine of the general formula:

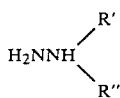  (XIX)

in which R' and R" represent identical or different alkyl radicals, is reacted with a product of the general formula (I) in which Y represents a radical of the general formula (II) defined as above, $R_1$ represents a hydrogen atom, R represents a pyridin-3-yl radical, m is equal to 1 and n is equal to 0, i.e. a product of the general formula:

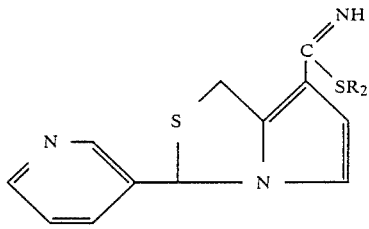  ($I_C$)

The reaction is generally carried out in an organic solvent such as ethanol, at a temperature of between 20° and 80° C.

The products of the general formula ($I_C$) can be prepared by reacting a product of the general formula (XI) defined as above with a product of the general formula (XII) in which the symbols are defined as above under (a).

The reaction is generally carried out in an organic solvent such as acetone or a mixture of acetone and dimethylformamide, at a temperature of between 0° and 50° C.

To obtain the products of the general formula (XIII) defined above under B in which the radical of the general formula (XVI) is defined as under ($a_2$), except that Q cannot represent a sulphur atom or an imino radical, ammonia or an amine of the general formula:

  (XX)

in which $R_5$ and $R_6$ are defined as above, is reacted with a product of the general formula (I) in which Y represents a carboxyl radical and the other symbols are defined as above under (b), i.e. a product of the general formula:

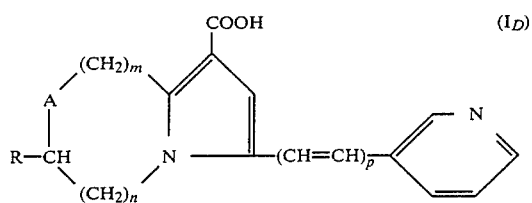  ($I_D$)

It is particularly advantageous to use the acid of the general formula ($I_D$) in an activated form such as the acid chloride, or to react it with N,N'-carbonyldiimidazole or an alkyl chloroformate before reaction with ammonia or the amine of the general formula (XX).

In general, it is preferable to react the acid chloride and to carry out the reaction in an organic solvent such as chloroform or methylene chloride, at a temperature of between 0° C. and the reflux temperature of the reaction mixture.

The acids of the general formula ($I_D$) can be prepared by hydrolysing the nitriles of the general formula ($I_A$) defined as above.

The hydrolysis can be carried out by any method known to those skilled in the art for converting a nitrile to an acid without affecting the rest of the molecule. It is generally advantageous to carry out the hydrolysis in a basic medium in a high-boiling alcohol, e.g. by means of potassium hydroxide in ethylene glycol, at between 100° C. and the reflux temperature of the reaction mixture.

The nitriles of the general formula ($I_A$) can be obtained by reacting a product of the general formula (IV) with a product of the general formula (V), as stated above.

To obtain the products of the general formula (XIII) defined as above under B in which the radical of the general formula (XVI) is such that Q represents an oxygen atom and M represents a radical of the general formula (XVII) in which $R_5$ and $R_6$ represent a hydrogen atom, a nitrile of the general formula ($I_A$), defined as above, is hydrolysed.

The hydrolysis can be carried out by any means known to those skilled in the art for converting a nitrile to an amide without affecting the rest of the molecule, in particular by heating in an alkaline medium in an organic solvent such as tert.-butanol, to a temperature of between 30° and 85° C.

To obtain the products of the general formula (XIII) defined as above under B in which the radical of the general formula (XVI) is such that Q represents an imino radical and M is defined as above under (a₂), ammonia or an amine of the general formula (XX) in which $R_5$ and $R_6$ are defined as above is reacted with a product of the general formula (I) in which Y represents a radical of the general formula (II) defined as above and the other symbols are defined as above under (b), i.e. a product of the general formula:

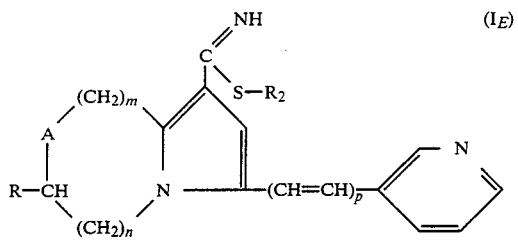

(I_E)

The reaction is generally carried out in an organic solvent such as chloroform, in the presence of a weak acid such as acetic acid, at a temperature of between 20° and 65° C.

The product of the general formula ($I_E$) can be prepared by reacting a product of the general formula (XI) with a product of the general formula (XII) in which the symbols are defined as above under (b).

The reaction is generally carried out in an organic solvent such as acetone or a mixture of acetone and dimethylformamide, at a temperature of between 0° and 50° C.

To obtain the products of the general formula (XIII) defined as above under (B) in which the radical of the general formula (XVI) is such that Q represents a sulphur atom and M represents a radical of the general formula (XVI) in which $R_5$ and $R_6$ represent a hydrogen atom and p is equal to 0, a nitrile of the general formula ($I_A$) defined as above is converted to a thioamide without affecting the rest of the molecule. It is particularly advantageous to react hydrogen sulphide with the nitrile of the general formula ($I_A$) in a solvent such as pyridine, in the presence of triethylamine, at a temperature of between 0° and 50° C.

To obtain the products of the general formula (XIII) defined as above under B in which the radical of the general formula (XVII) is such as defined above under (b₂), a dialkylhydrazine of the general formula (XIX) defined as above is reacted with a product of the general formula ($I_E$) defined as above.

The reaction is generally carried out in an organic solvent such as ethanol, at a temperature of between 20° and 80° C.

To obtain the products of the general formula (XIII) defined as above under B in which the radical of the general formula (XVI) is such that Q represents an oxygen atom and M represents a radical of the general formula (XVII) in which $R_5$ represents a hydrogen atom and $R_6$ represents an alkyl radical containing 1 to 5 carbon atoms, which is substituted by a hydroxyalkylamino radical, it being understood that the alkyl radical and the alkyl portion of the hydroxyalkylamino radical contain the same number of carbon atoms, an aminoalcohol of the general formula:

$$H_2N-G-OH \quad (XXI)$$

in which G represents an alkylene radical containing 1 to 5 carbon atoms, is reacted with a nitrile of the general formula ($I_A$) defined as above.

The reaction is generally carried out in an excess of aminoalcohol of the general formula (XXI), in the presence of lithium chloride, at a temperature of between 100° C. and the reflux temperature of the reaction mixture.

To obtain the products of the general formula (XIII) defined as above under B in which the radical of the general formula (XVI) is defined as above under (c₂), a product of the general formula:

$$H_2NCH_2CH_2-T-H \quad (XXII)$$

in which T represents a sulphur atom or an imino radical, is reacted with a nitrile of the general formula ($I_A$) defined as above.

The reaction is generally carried out in an organic solvent such as an alcohol, or in an excess of product of the general formula (XXII), at a temperature of between 60° C. and the reflux temperature of the reaction mixture.

The new products of the general formula (I) and the therapeutically active products of the general formula (XIII) can be purified by the usual known methods, e.g. crystallisation, chromatography or successive extractions in acidic and basic media.

The new products of the general formula (I) and the therapeutically active products of the general formula (XIII) can be converted to addition salts with acids by reaction with an acid in an organic solvent such as an alcohol, a ketone, an ether or a chlorinated solvent. The salt formed precipitates, if necessary after concentration of its solution; it is separated off by filtration or decantation.

The new products of the general formula (I) in which Y represents a carboxyl radical, and the therapeutically active products of the general formula (XIII) containing an acid group in their molecule, can be converted to metal salts or to addition salts with nitrogen bases by any method known to those skilled in the art for carrying out this salt formation without affecting the rest of the molecule.

The therapeutically active products of the general formula (XIII) defined as above under A have valuable pharmacological properties coupled with a low toxicity. They have been shown to be active at concentrations of less than 50 mg/liter in the test for measuring the in vitro inhibitory activity towards the platelet aggregation caused by 1-0-octadecyl 2-0-acetyl ns-glycero-3-phosphorylcholine (P.A.F.- acether) according to the technique of G. V. R. BORN et al. J. Physiol. 168, 178 (1963).

Their toxic dose (expressed by the $LD_{50}$) in mice is generally between 300 and 900 mg/kg, administered orally.

These properties make it possible to consider the treatment of allergic and inflammatory complaints and, in general, complaints in which the physiopathological role of P.A.F. acether can be incriminated.

The therapeutically active products of the general formula (XIII) defined as above under B have valuable pharmacological properties making them useful in the prophylactic and therapeutic treatment of thrombotic complaints. They have been shown to be active at concentrations of less than 50 mg/liter in the test for measuring the in vitro inhibitory activity towards the platelet aggregation caused by collagen, according to the technique of G. V. R. BORN et al., [J. Physiol., 168, 178 (1963)].

Their $LD_{50}$ is generally between 300 and 900 mg kg, administered orally to mice.

For their medicinal use, the therapeutically active products of the general formula (XIII) can be employed as such or in the form of pharmaceutically acceptable salts, i.e. salts which are non-toxic at the use doses.

Examples of pharmaceutically acceptable salts which may be mentioned are the addition salts with mineral acids, such as the hydrochlorides, sulphates, nitrates and phosphates, or with organic acids, such as the acetates, propionates, succinates, benzoates, fumarates, maleates, methanesulphonates, isethionates, theophylline-acetates, salicylates, phenolphthalinate and methylene-bis-$\beta$-oxynaphthoates, or substitution derivatives of these compounds. If they are able to exist, there may also be mentioned the salts with alkali metals, such as the sodium, potassium or lithium salts, or with alkaline earth metals, such as the calcium or magnesium salts, and the addition salts with organic bases, such as the ethanolamine or lysine salts.

As salts to which the products of the general formula (I) can be converted, there may be mentioned the therapeutically acceptable salts listed above for the products of the general formula (XIII).

The examples which follow, which are given without implying a limitation, show how the invention can be put into practice. The application examples, which are also given without implying a limitation, show how the products of the invention can be used in practice for converting them to therapeutically active products of the general formula (XIII).

EXAMPLE 1

3-(Pyridin-3-yl)-1H,3H-pyrrolo[1,2-c]thiazole-7-carbonitrile (48 g) is added to a solution of potassium hydroxide pellets (41.7 g) in ethylene glycol (400 cc). The reaction mixture is heated at a temperature of the order of 150° C. for 6 hours 30 minutes. After stirring for 16 hours at a temperature of the order of 20° C., the solvent is evaporated off under reduced pressure (5 mm Hg; 0.7 kPa) at a temperature of the order of 100° C. The residue is dissolved in distilled water (380 cc). The solution obtained is treated with decolourising charcoal (0.5 g) and filtered, and the filtrate is brought to a pH of the order of 4 by adding a concentrated aqueous solution of hydrochloric acid, the temperature being kept at about 20° C. The crystals which have appeared are filtered off, washed 3 times with distilled water (600 cc in total) and then dried under reduced pressure (20 mm Hg; 2.7 kPa) at a temperature of the order of 20° C., in the oresence of potassium hydroxide pellets. This gives a crude product (49.5 g) melting at 177° C. This product is dissolved in boiling ethanol (840 cc). The solution obtained is treated with decolourising charcoal (0.5 g) and then filtered hot; the filtrate is cooled at a temperature of the order of 4° C. for 1 hour. The crystals which have appeared are filtered off, washed 3 times with ethanol cooled to a temperature of the order of 4° C. (45 cc in total) and then 3 times with diethyl ether (90 cc in total) and dried under reduced pressure (20 mm Hg; 2.7 kPa) at a temperature of the order of 20° C., in the presence of potassium hydroxide pellets. This gives 3-(pyridin-3-yl)-1H,3H-pyrrolo[1,2-c]thiazole-7-carboxylic acid (36.6 g) in the form of cream crystals melting at 178° C.

The 3-(pyridin-3-yl)-1H,3H-pyrrolo[1,2-c]thiazole-7-carbonitrile can be obtained in the following manner:

A mixture of 3-formyl-2-(pyridin-3-yl)-thiazolidine-4-carboxylic acid (249.4 g), 2-chloroacrylonitrile (457 g) and hydroquinone (0.2 g) in acetic anhydride (1760 cc) is heated at a temperature of between 110° C. and 117° C. for 70 minutes. The solvent is then evaporated off under reduced oressure (20 mm Hg; 2.7 kPa) at a temperature of between 50° C. and 80° C. The residue is taken up in distilled water (400 cc); the suspension obtained is brought to a pH of the order of 10 by adding a 5 N aqueous solution of sodium hydroxide and then extracted 4 times with methylene chloride (2500 cc in total). The organic extracts are combined, washed 3 times with distilled water (1500 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 40° C. The residue obtained is dissolved in a mixture of ethyl acetate (250 cc) and a 1.8 N aqueous solution of hydrochloric acid (500 cc). The organic phase is separated off by decantation and extracted twice with distilled water (200 cc in total). The aqueous extracts are combined, washed 5 times with ethyl acetate (500 cc in total), treated with decolourising charcoal (0.5 g) and filtered; the filtrate is brought to a pH of the order of 10 by adding a 10 N aqueous solution of sodium hydroxide at a temperature of the order of 4° C. and then extracted 3 times with ethyl acetate (650 cc in total). The organic extracts are combined, washed 3 times with distilled water (450 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 40° C. This gives a crude product (71.2 g). This product is dissolved in boiling propan-2-ol (150 cc) and the solution obtained is treated with decolourising charcoal (0.5 g) and then filtered hot; the filtrate is cooled at a temperature of the order of 4° C. for 1 hour. The crystals which have appeared are filtered off, washed 3 times with propan-2-ol cooled to a temperature of the order of 4° C. (30 cc in total) and 3 times with isopropyl ether (60 cc in total) and then dried under reduced pressure (20 mm Hg; 2.7 kPa) at a temperature of the order of 20° C., in the presence of potassium hydroxide pellets. This gives 3-(pyridin-3-yl)-1H,3H-pyrrolo[1,2-c]thiazole-7-carbonitrile (44 g) in the form of ochre-coloured crystals melting at 117° C.

The 3-formyl-2-(oyridin-3-yl)-thiazolidine-4-carboxylic acid can be obtained in the following manner:

2-(Pyridin-3-yl)-thiazolidine-4-carboxylic acid (250 g) is added to formic acid (1200 cc), the temperature of the reaction medium being kept below 25° C. Acetic anhydride (875 g) is added to the solution thus obtained in the course of 1 hour, the temperature being kept at between 10° C. and 18° C.

After stirring for 20 hours at a temperature of the order of 20° C., the solvent is evaporated off under reduced pressure (20 mm Hg; 2.7 kPa) at a temperature of the order of 60° C., the residue is taken up in ethanol (1000 cc) and the mixture is heated at the boil for 5 minutes and then cooled at a temperature of the order of 4° C. for 1 hour; the crystals which have appeared are filtered off, washed 3 times with ethanol (600 cc in total) and then 3 times with diethyl ether (300 cc in total) and dried under reduced pressure (20 mm Hg; 2.7 kPa) at a temperature of the order of 20° C., in the presence of potassium hydroxide pellets. This gives 3-formyl-2-(pyridin-3-yl)-thiazolidinr-4-carboxylic acid (234.5 g) in the form of cream crystals melting at 214° C.

The 2-(pyridin-3-yl)-thiazolidine-4-carboxylic acid can be orepared according to A BANASHEK and M. I. SHCHUKINA, J. Gen. Chem. U.S.S.R., 31, 1374 (1961); Chem. Abstr. 55, 24739 h (1961).

EXAMPLE 2

A suspension of 3-(pyrioin-3-yl)-1H,3H-pyrrolo-[1,2-c]thiazole-7-carbothioamide (7 g) and methyl iodide (4.2 g) in acetone (250 cc) is stirred at a temperature of the order of 20° C. for 16 hours. Dimethylformamide (50 cc) is then added to the suspension and stirring is continued for a further 3 days. The crystals are then filtered off, washed 3 times with acetone (90 cc in total) and dried under reduced pressure (20 mm Hg; 2.7 kPa) at a temoerature of the order of 20° C., in the presence of potassium hydroxide pellets. This gives S-methyl 3-(pyridin-3-yl)-1H-3H-pyrrolo[1 .2-c]thiazole-7-thiocarboximidate hydroiodide (9.5 g) in the form of yellow crystals melting at 193°–194° C.

The 3-(pyridin-3-yl)-1H,3H-pyrrolo[1,2-c]thiazole-7-carbothioamide is prepared in the following manner:

3-(Pyridin-3-yl)-1H,3H-pyrrolo[1,2-c]thiazole-7-carboxamide (8.1 g) is added to pyridine (100 cc) saturated at a temperature of the order of 20° C. with a gaseous stream of hydrogen sulphide. The suspension obtained is treated with phosphorus pentasulphide (7.3 g) and then heated at the boil for 2 hours under a gaseous stream of hydrogen sulphide. The solution obtained is cooled to a temperature of the order of 20° C. and is then poured into distilled water (1200 cc). The suspension obtained is keot at a temperature of the order of 4° C. for 16 hours. The crystals are filtered off, washed 5 times with distilled water (500 cc in total), 5 times with ethanol (25 cc in total) and 5 times with diethyl ether (100 cc in total) and then dried under reduced pressure (20 mm Hg; 2.7 kPa) at a temperature of the order of 20° C., in the presence of potassium hydroxide pellets. This gives a crude product (7.7 g) melting at 205° C. This product is dissolved in boiling butan-1-ol (180 cc). The solution obtained is cooled at a temperature of the order of 4° C. for 1 hour. The crystals which have appeared are filtered off, washed 3 times with butan-1-ol cooled to a temoerature of the order of 4° C. (15 cc in total) and 3 times with diethyl ether (60 cc in total) and then dried under reduced pressure (20 mm Hg; 2.7 kPa) at a temperature of the order of 20° C., in the presence of potassium hydroxide pellets. This gives 3-(pyridin-3-yl)-1H,3H-pyrrolo[1,2-c]thiazole-7-carbothioamide (7.1 g) in the form of cream crystals melting at 205° C.

The 3-(pyridin-3-yl)-1H,3H-pyrrolo[1,2-c]thiazole-7-carboxamide is prepared in the following manner:

A mixture of 3-(oyridin-3-yl)-1H,3H-pyrrolo[1,2-c]thiazole-7-carbonitrile (13.6 g) and oowdered potassium hydroxide (21 g) in tert.-butyl alcohol (150 cc) is heated for 3 hours 15 minutes at a temperature of the order of 85° C., with stirring. The solvent is then evaporated off under reduced pressure (20 mm Hg; 2.7 kPa) at a temperature of the order of 40° C., the residue is then resuspended in distilled water (500 cc) and the suspension is stirred for 5 minutes at a temperature of the order of 20° C.; the crystals which have appeared are filtered off, washed 5 times with distilled water (500 cc in total), 3 times with ethanol (60 cc in total) and then 3 times with diethyl ether (60 cc in total) and dried under reduced pressure (20 mm Hg; 2.7 kPa) at a temperature of the order of 20° C., in the presence of potassium hydroxide pellets. This gives a crude product (12.1 g) melting at 208° C. This product, combined with the product prepared in the same manner in another earlier operation. (2.2 g), is dissolved in boiling ethanol (800 cc). The solution obtained is treated with decolourising charcoal (0.5 g) and then filtered hot. The filtrate is cooled for 1 hour at a temperature of the order of 4° C.; the crystals which have appeared are filtered off, washed 3 times with ethanol cooled to a temperature of the order of 4° C. (30 cc in total) and dried under reduced pressure (20 mm Hg; 2.7 kPa) at a temperature of the order of 20° C., in the presence of potassium hytdroxide pellets. This gives 3-(pyridin-3-yl)-1H,3H-pyrrolo[1,2-c]thiazole-7-carboxamide (10.7 g) in the form of white crystals melting at 210° C.

The 3-(pyridin-3-yl)-1H,3H-pyrrolo[1,2-c]thiazole-7-carbonitrile is prepared as in Example 1.

EXAMPLE 3

A suspension of N-nicotinoylthiazolidine-4-carboxylic acid (403 g) in a mixture of 2-chloroacrylonitrile (1,350 cc) and acetic anhydride (1,750 cc) is heated at 90° C. for 2 hours 40 minutes. During this period, the mixture is seen to pass through a clear homogeneous phase after 30 minutes, this being followed by precipitation 10 minutes later. After cooling at a temperature of the order of 4° C. for 16 hours, the crystals which have appeared are filtered off, washed twice with acetic anhydride (200 cc in total) and 3 times with acetone (300 cc in total) and dried under reduced pressure (20 mm Hg; 2 7 kPa) at a temperature of the order of 20° C., in the presence of potassium hydroxide pellets. The product thus obtained is suspended in a 2N aqueous solution of sodium hydroxide (2,400 cc). After stirring at a temperature of the order of 20° C. for 1 hour 30 minutes, the crystals which have appeared are filtered off, washed 5 times with distilled water (1,250 cc in total), 3 times with ethanol (1,200 cc in total) and 3 times with diethyl ether (900 cc in total) and dried under reduced pressure (20 mm Hg; 2.7 kPa) at a temperature of the order of 20° C., in the presence of potassium hydroxide pellets. This gives 5-(pyridin-3-yl)-1H,3H-pyrrolo[1,2-c]thiazole-7-carbonitrile (159.7 g) in the form of cream crystals melting at 170° C.

The N-nicotinoylthiazolidine-4-carboxylic acid can be obtained in the following manner:

Nicotinoyl chloride hydrochloride (534 g) is added in the course of 1 hour, at a temperature of between 30° and 52° C., to a solution of thiazolidine-4-carboxylic acid (400 g) and triethylamine (613 g) in chloroform (4,500 cc). The solution obtained is heated at a temperature of the order of 64° C. for 4 hours. After stirring at a temperature of the order of 20° C. for 16 hours, the crystals which have appeared are filtered off, washed 3 times with chloroform (1,500 cc in total) and then 3 times with diethyl ether (1,500 in total) and dried under reduced pressure (20 mm Hg; 2.7 kPa) at a temperature of the order of 20° C., in the presence of potassium hydroxide pellets. This gives N-nicotinoylthiazolidine-4-carboxylic acid (403 g) in the form of white crystals melting at 190° C..

EXAMPLE 4

A suspension of N-nicotinoyl-L-proline (44 g) in a mixture of 2-chloroacrylonitrile (160 cc) and acetic anhydride (200 cc) is heated gradually to 90° C. After the reactants have dissolved in the reaction medium, precipitation is observed, giving rise to a suspension. The heating of the suspension is continued for 3 hours 30 minutes at a temperature of the order of 90° C. After cooling at a temperature of the order of 4° C. for 1 hour, the crystals which have appeared are filtered off, washed twice with acetic anhydride (50 cc in total) and 3 times in acetone (300 cc in total) and dried under reduced pressure (20 mm Hg; 2.7 kPa) at a temperature of the order of 20° C., in the presence of potassium hydroxide pellets. The product thus obtained is taken up in a 1N aqueous solution of sodium hydroxide (500 cc). The oil which has appeared is dissolved in ethyl acetate (250 cc). The organic phase is separated off by decantation and the aqueous phase is extracted 3 times with ethyl acetate (750 cc in total). The organic extracts are combined, washed 3 times with distilled water (750 cc in total), dried over anhydrous potassium carbonate, treated with decolourising charcoal (1 g) and filtered, and the filtrate is concentrated to dryness under reduced pressure (20 mm Hg; 2.7 kPa) at a temperature of the order of 60° C. This gives a crude product (25.2 g). This product is chromatographed on a column of diameter 4 cm, containing silica (0.063–0.2 mm) (250 g), elution being carried out with ethyl acetate and 400 cc fractions being collected. The first two fractions are discarded and the next three fractions are combined and concentrated to dryness under reduced pressure (20 mm Hg; 2.7 kPa) at a temperature of the order of 60° C. This gives a product (21 g). This product is dissolved in boiling ethanol (100 cc). The solution obtained is cooled at a temperature of the order of 4° C. for 1 hour. The crystals which have appeared are filtered off and washed 3 times with ethanol cooled to a temperature of the order of 4° C. (30 cc in total) and then 3 times with isopropyl ether (150 cc in total). This gives 5-(pyridin-3-yl)-2,3-dihydro-1H-pyrrolizine-7-carbonitrile (16.1 g) in the form of cream crystals melting at 112° C.

The N-nicotinoyl-L-proline can be prepared according to F. COUSTOU and B. BELLEGARDE, West German Pat. No. 2,537,590.

EXAMPLE 5

A suspension of N-[3-(pyridin-3-yl)-acryloyl]-thiazolidine-4-carboxylic acid (13.2 g) in a mixture of 2-chloroacrylonitrile (39.6 cc) and acetic anhydride (52 cc) is heated at about 83° C. for 4 hours. After cooling for 16 hours at a temperature of the order of 4° C., the crystals which have appeared are filtered off and washed twice with acetic anhydride (10 cc in total) and three times with acetone (60 cc in total). The product thus obtained is suspended in distilled water (70 cc). The mixture is brought to a pH of the order of 10 by adding a 2N aqueous solution of sodium hydroxide. After stirring at a temperature of the order of 20° C. for one hour, the crystals which have appeared are filtered off, washed three times with distilled water (60 cc in total), twice with acetone (40 cc in total) and twice with diethyl ether (40 cc in total) and dried under reduced pressure (20 mm Hg; 2.7 kPa) at a temperature of the order of 20° C., in the presence of potassium hydroxide pellets. This gives a mixture of 6-cyano and 7-cyano-5-[2-(pyridin-3-yl)-vinyl]-1H,3H-pyrrolo[1,2-c]thiazole in the form of beige crystals melting at 170° C.

The N-[3-(pyridin-3-yl)-acryloyl]-thiazolidine-4-carboxylic acid can be obtained in the following manner:

3-(Pyridin-3-yl)-acryloyl chloride hydrochloride (34.1 g) is added in the course of 30 minutes, at a temperature of between 20° C. and 35° C., to a solution of thiazolidine-4-carboxylic acid (22.5 g) in a mixture of triethylamine (47 cc) and chloroform (250 cc). The reaction mixture is heated under reflux for 16 hours and then concentrated to dryness under reduced pressure (20 mm Hg; 2.7 kPa). The residue obtained, treated with distilled water (500 cc), is heated to the reflux temperature. After the addition of decolourising charcoal (1 g), the mixture is filtered hot and the filtrate is cooled at 4° C. for 16 hours. The crystals which have appeared are filtered off, washed twice with distilled water (100 cc in total) and once with ethanol (30 cc) and then dried under reduced pressure (20 mm Hg; 2.7 kPa) at a temperature of the order of 20° C., in the presence of potassium hydroxide pellets. This gives a crude product (21.1 g) melting at 173° C.. This product is dissolved in boiling ethanol (400 cc). The solution obtained is treated with decolourising charcoal (1 g) and filtered hot. The filtrate is cooled at a temperature of the order of 4° C. for 16 hours. The crystals which have appeared are filtered off, washed twice with ethanol (40 cc) in total and dried under reduced pressure (20 mm Hg; 2.7 kPa) at a temperature of the order of 20° C., in the presence of potassium hydroxide pellets. This gives N-[3-(pyridin-3-yl)-acryloyl]-thiazolidine-4-carboxylic acid (13.5 g) melting at 176° C.

The 3-(pyridin-3-yl)-acryloyl chloride hydrochloride can be obtained in the following manner:

Thionyl chloride (200 cc) is added in the course of 15 minutes to 3-(pyridin-3-yl)-acrylic acid (50 g). The reaction mixture is then heated under reflux for 5 hours. The excess thionyl chloride is distilled and the reaction mixture is then concentrated to dryness after the addition of anhydrous cyclohexane (300 cc). This last operation is repeated once. The residue obtained is treated with chloroform (200 cc) and the mixture is heated under reflux for 15 minutes. After cooling, the crystals are filtered off, washed once with chloroform (50 cc) and twice with hexane (200 cc in total) and then dried under reduced pressure (20 mm Hg; 2.7 kPa) at a temperature of the order of 20° C., in the presence of potassium hydroxide pellets. This gives 3-(pyridin-3-yl)acryloyl chloride hydrochloride (55 g) melting at 187° C.

The 3-(pyridin-3-yl)-acrylic acid can be prepared according to L. PANNIZZON, Helv. Chim. Acta, 24, 24E (1941).

EXAMPLE 6

A suspension of N-nicotinoyl-2-methylthiazolidine-4-carboxylic acid (36.3 g) in a mixture of 2-chloroacrylonitrile (115 cc) and acetic anhydride (200 cc) is heated at a temperature of the order of 90° C. for 3 hours. The solution obtained is concentrated to dryness under reduced pressure (20 mm Hg; 2.7 kPa) at a temperature of the order of 70° C. and the residue obtained is taken up in distilled water (200 cc). The suspension obtained is brought to a pH of the order of 10 by adding a 10N aqueous solution of sodium hydroxide (80 cc), the reaction mixture being kept at a temperature of the order of 20° C. The suspension obtained is treated with methylene chloride (250 cc) and stirred at a temperature of the order of 20° C. for 16 hours. The organic phase is separated off by decantation and the aqueous phase is extracted 5 times with methylene chloride (500 cc in total). The organic extracts are combined and washed 5 times with distilled water (500 cc in total) and 5 times with a 2N aqueous solution bf hydrochloric acid (400 cc in total). The aqueous phase is separated off be decantation, treated with decolourising charcoal (0.5 g) and filtered, and the filtrate is brought to a pH of the order of 10 by adding a 10N aqueous solution of sodium hydroxide and extracted 5 times with methylene chloride (500 cc in total). The organic extracts are combined, dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a crude product (19.3 g). This product is chromatographed on a column of diameter 6 cm, containing silica (0.04–0.063 mm) (480 g). Elution is carried out with a mixture of cyclohexane and ethyl acetate (50/50 by volume) under a pressure of 0.5 bar (51 kPa), 200 cc fractions being collected. The first 8 fractions are discarded and the next 8 fractions are combined and concentrated to dryness under reduced pressure (20 mm Hg; 2.7 kPa) at a temperature of the order of 50° C.. This gives a mixture of 6-cyano and 7-cyano-3-methyl-5-(pyridin-3-yl)-1H,3H-pyrrolo[1,2-c]thiazole (17.6 g), in a ratio of 50/50 (according to the NMR spectrum), in the form of a yellow oil.

[Rf=0.35 and 0.4; chromatography on a thin layer of silica gel; solvent: cyclohexane/ethyl acetate (50/50 by volume)].

The N-nicotinoyl-2-methylthiazolidine-4-carboxylic acid can be prepared in the following manner:

Nicotinoyl chloride hydrochloride (53.4 g) is added in the course of 25 minutes, at a temperature of between 20° C. and 47° C., to a suspension of 2-methylthiazolidine-4-carboxylic acid (44.1 g) and triethylamine (61.8 g) in chloroform (500 cc). The suspension obtained is heated at a temperature of the order of 65° C. for 1 hour 45 minutes and the solution obtained is then stirred at a temperature of the order of 20° C. for 16 hours. The solvent is evaporated off under reduced pressure (20 mm Hg; 2.7 kPa) at a temperature of the order of 50° C. and the residue obtained is suspended in acetone (300 cc). After stirring for 2 hours at a temperature of the order of 20° C., the crystals which have appeared are filtered off, washed twice with acetone (400 cc in total) and dried under reduced pressure (20 mm Hg; 2.7 kPa) at a temperature of the order of 20° C., in the presence of potassium hydroxide pellets. The solid obtained is suspended in distilled water (250 cc) and the crystals which have appeared are filtered off, washed 3 times with distilled water (450 cc in total) and 3 times with acetone (60 cc in total) and dried under reduced pressure (20 mm Hg; 2.7 kPa) at a temperature of the order of 20° C., in the presence of potassium hydroxide pellets. This gives N-nicotinoyl-2-methylthiazolidine-4-carboxylic acid (36.5 g) in the form of cream crystals melting at 190° C.

The 2-methylthiazolidine-4-carboxylic acid can be prepared according to H. T. NAGASAWA, D. J. W. GOON, R. T. ZERA and D. L. YUZON, J. Med. Chem., 25, 489 (1982).

EXAMPLE 7

A suspension of N-nicotinoyl-2-phenylthiazolidine-4-carboxylic acid (45.2 g) in a mixture of 2-chloroacrylonitrile (115 cc) and acetic anhydride (180 cc) is heated at a temperature of the order of 90° C. for 3 hours and the solution obtained is stirred at temperature of the order of 20° C. for 16 hours. The solvent is evaporated off under reduced pressure (20 mm Hg; 2.7 kPa) at a temperature of the order of 60° C. and the residue is taken up at a temperature of the order of 4° C. in a mixture of distilled water (300 cc), a 10N aqueous solution of sodium hydroxide (400 cc) and ethyl acetate (500 cc). The organic phase is separated off by decantation and the aqueous phase is extracted 3 times with ethyl acetate (1,500 cc in total) and 4 times with methylene chloride (2,000 cc in total). The organic extracts are combined, washed 4 times with distilled water (1,000 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a crude product (33.8 g). This product is chromatographed on a column of diameter 6 cm, containing silica (0.04–0.063 mm) (480 g). Elution is carried out with a mixture of cyclohexane and ethyl acetate (50/50 by volume) under a pressure of 0.5 bar (51 kPa), 100 cc fractions being collected. The first 17 fractions are discarded and the next 14 fractions are combined and concentrated to dryness under reduced pressure (20 mm Hg; 2.7 kPa) at a temperature of the order of 60° C. This gives a mixture of 6-cyano and 7-cyano-3 phenyl 5-(pyridin-3-yl)-1H,3H-pyrrolo[1,2-c]thiazole (11.3 g), in a ratio of 20/80 (according to the NMR spectrum), in the form of a brown oil.

[Rf=0.35 and 0.4; chromatography on a thin layer of silica gel; solvent: cyclohexane/ethyl acetate (50/50 by volume)].

The N-nicotinoyl-2-phenylthiazolidine-4-carboxylic acid can be prepared in the following manner:

Nicotinoyl chloride hydrochloride (88.1 g) is added in the course of 20 minutes, at a temperature of between 32° and 54° C., to a solution of 2-phenylthiazolidine-4-carboxylic acid (94.2 g) and triethylamine (100 g) in chloroform (1,120 cc). The solution obtained is heated at a temperature of the order of 63° C. for 5 hours and is then stirred at a temperature of the order of 20° C. for 16 hours. A product crystallises. The suspension is cooled at a temperature of the order of 4° C. for 1 hour. Tne crystals which have appeared are filtered off, washed 3 times with chloroform (300 cc in total) and dried under reduced pressure (20 mm Hg; 2.7 kPa) at a temperature of the order of 20° C., in the presence of potassium hydroxide pellets. This gives a crude product (145 g) melting at 150° C. This product is suspended in distilled water (750 cc). Thc crystals are filtered off, washed 3 times with distilled water (750 cc in total) and dried in air. This gives a product (90.9 g) melting at 182° C. This product (15 g) is dissolved in boiling ethanol (200 cc). The solution obtained is treated with decolourising charcoal (0.5 g) and filtered hot. The filtrate is cooled at a temperature of the order of 4° C. for 1 hour. The crystals which have appeared are filtered off, washed twice with ethanol (50 cc in total) and 3 times with diethyl ether (75 cc in total) and dried under reduced pressure (20 mm Hg; 2.7 kPa) at a temperature of the order of 20° C., in the presenc(e of potassium hydroxide pellets. This gives N-nicotinoyl-2-phenylthiazolidine-4-carboxylic acid (11.4 g) in the form of white crystals melting at 186° C.

The 2-phenylthiazolidine-4-carboxylic acid can be prepared according to R. RIEMSCHNEIDER and G. A. HOYER, Z. Naturforsch, 17 B, 765 (1962).

EXAMPLE 8

A suspension of N-nicotinoylpiperidine-2-carboxylic acid (14.7 g) in a mixture of 2-chloroacrylonitrile (50 cc) and acetic anhydride (65 cc) is heated at a temperature of the order of 90° C. for 4 hours. After stirring for 16 hours at a temperature of the order of 20° C., the crystals are filtered off, washed 3 times with acetic anhydride (75 cc in total) and dried under reduced pressure (20 mm Hg; 2.7 kPa) at a temperature of the order of 20° C., in the presence of potassium hydroxide pellets. The product thus obtained (10 g) is dissolved in distilled water (100 cc). After the addition of a 10N aqueous solution of sodium hydroxide (50 cc) at a temperature of the order of 10° C., a suspension is obtained, which is stirred at a temperature of the order of 20° C. for 1 hour and then extracted 3 times with ethyl acetate (450 cc in total). The organic extracts are combined, washed 3 times with distilled water (300 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a product (8.8 g), which is chromatographed on a column of diameter 6 cm, containing silica (0.04–0.063 mm) (480 g), elution being carried out with ethyl acetate under a pressure of 0.5 bar (51 kPa) and 100 cc fractions being collected. The first 14 fractions are discarded and the next 6 fractions are combined and concentrated to dryness under reduced pressure (20 mm Hg; 2.7 kPa) at a temperature of the order of 60° C. This gives 3-(pyridin-3-yl)-5,6,7,8-tetrahydroindolizine-1-carbonitrile (5.2 g) in the form of brown crystals melting at 112° C.

The N-nicotinoylpiperidine-2-carboxylic acid can be prepared in the following manner:

A solution of ethyl N-nicotinoylpiperidine-2-carboxylate (34.1 g) in a mixture of a 2N aqueous solution of sodium hydroxide (130 cc) and ethanol (325 cc) is stirred at a temperature of the order of 20° C. for 16 hours. The solvent is then evaporated off under reduced pressure (20 mm Hg; 2.7 kPa) at a temperature of the order of 60° C. The residue obtained is dissolved in distilled water (250 cc). The turbid solution obtained is treated with decolourising charcoal (0.5 g) and filtered. The filtrate, kept at a temperature of 20° C., is brought to a pH of the order of 3 by adding a 4N aqueous solution of hydrochloric acid (80 cc). The suspension obtained is stirred at a temperature of the order of 20° C. for 1 hour and the crystals are filtered off, washed 4 times with distilled water (200 cc in total), 3 times with acetone (150 cc in total) and once with diethyl ether (50 cc) and then dried under reduced pressure (20 mm Hg; 2.7 kPa) at a temperature of the order of 20° C., in the presence of potassium hydrbxide pellets. This gives N-nicotinoylpiperidine-2-carboxylic acid (14.8 g) in the form of white crystals melting at 194° C.

The ethyl N-nicotinoylpiperidine-2-carboxylate can be prepared in the following manner:

Triethylamine (182 g) is initially added, at a temperature of between 20° C. and 31° C., to a solution of ethyl piperidine-2-carboxylate (72.9 g) in chloroform (1,120 cc), this being followed, in the course of 35 minutes, at a temperature of between 26° C. and 50° C., by nicotinoyl chloride hydrochloride (160.2 g) The suspension obtained is stirred at a temperature of the order of 20° C. for 16 hours and then washed 5 times with distilled water (1,5000 cc in total), dried over anhydrous magnesium sulphate treated with decolourising charcoal (0.5 g) and filtered, and the filtrate is concentrated to dryness under reduced pressure (20 mm Hg; 2.7 kPa) at a temperature of the order of 60° C. This gives a crude product (174 g), which is chromatographed on a column of diameter 8 cm, containing silica (0.063–0.2 mm) (1,740 g), elution being carried out with mixtures of cyclohexane and ethyl acetate and 1,000 cc fractions being collected. The first 5 fractions from elution with a mixture of cyclohexane and ethyl acetate (80/20 by volume), the next 5 fractions from elution with a mixture of cyclohexane and ethyl acetate (70/30 by volume), the next 7 fractions from elution with a mixture of cyclohexane and ethyl acetate (60/40 by volume) and the next fraction from elution with a mixture of cyclohexane and ethyl acetate (50/50 by volume) are discarded. The next 8 fractions from elution with a mixture of cyclohexane and ethyl acetate (50/50 by volume) and the next 7 fractions from elution with pure ethyl acetate are combined and concentrated to dryness under reduced pressure (20 mm Hg; 2.7 kPa) at a temperature of the order of 60° C. This gives ethyl N-nicotinoylpiperidine-2-carboxylate (99.3 g) in the form of an orange oil.

(Rf=0.46; chromatography on a thin layer of silica gel; eluent: ethyl acetate).

EXAMPLE 9

A suspension of N-nicotinoyl-2,3,5,6,tetrahydro-1,4-thiazine-3-carboxylic acid (27.9 g) in a mixture of 2-chloroacrylonitrile (89 cc) and acetic anhydride (117 cc) is heated gradually. When the temperature reaches 70° C., the temperature is seen to rise to 90° C. and the suspended material dissolves, this being followed, after 5 minutes at this temperature, by crystallisation, producing a suspension. Heating is continued at a temperature of the order of 90° C. for 2 hours and the reaction mixture is then cooled to a temperature of the order of 20° C. The crystals are filtered off, washed 3 times with acetic anhydride (75 cc in total) and then 3 times with acetone (150 cc in total) and dried under reduced pressure (20 mm Hg; 2.7 kPa) at a temperature of the order of 20° C., in the presence of potassium hydroxide pellets. This gives a product (6.3 g). This product is suspended in distilled water (100 cc). The suspension obtained is treated with a 5N aqueous solution of sodium hydroxide (50 cc) and then extracted 3 times with ethyl acetate (300 cc in total). The organic extracts are combined, washed 3 times with distilled water (150 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives 6-(pyridin-3-yl)-3,4-dihydro-1H-pyrrolo[2,1-c]-1,4-thiazine-8-carbonitrile (5 g) in the form of light orange crystals melting at 150° C.

The N-nicotinoyl-2,3,5,6-tetrahydro-1,4-thiazine-3-carboxylic acid can be prepared in the following manner:

A solution of ethyl N-nicotinoyl-1,4-thiazine-3-carboxylate (2.8 g) in a mixture of ethanol (25 cc) and a 2N aqueous solution of sodium hydroxide (10 cc) is stirred at a temperature of the order of 20° C. for 3 hours. The solvent is then evaporated off under reduced pressure (20 mm Hg; 2.7 kPa) at a temperature of the order of 50° C. The product obtained is dissolved in distilled water (50 cc) and purified by passing this solution over DOWEX 50WX-2 resin (50-100 mesh) (30 g) contained in a column of diameter of 1.6 cm. The first fraction from elution with distilled water, the second fraction from elution with methanol and the third fraction from elution with distilled water are discarded, as are also the next 2 fractions from elution with a 2% strength (v/v) aqueous solution of pyridine. The next 2 fractions from elution with a 2% strength (v/v) aqueous solution of pyridine are combined and concentrated to dryness under reduced pressure (20 mm Hg; 2.7 kPa) at a temperature of the order of 50° C. This gives a crude product (2.3 g). This product is dissolved in boiling methanol (50 cc) and the solution obtained is cooled at a temperature of the order of 4° C. for 1 hour. The crystals which have appeared are filtered off, washed twice with methanol (100 cc in total) and then 3 times with isopropyl ether (45 cc in total) and dried under reduced pressure (20 mm Hg; 2.7 kPa) at a temperature of the order of 20° C., in the presence of potassium hydroxide pellets. This gives N-nicotinoyl-2,3,5,6-tetrahydro-1,4-thiazine-3-carboxylic acid (1 5 g) in the form of white crystals melting at 212° C..

The ethyl N-nicotinoyl-2,3,5,6,-tetrahydro-1,4-thiazine-3-carboxylate can be obtained in the following manner:

Nicotinoyl chloride hydrochloride (8.9 g) is added in the course of 25 minutes, at a temperature of between 24° C. and 38° C., to a solution of ethyl 2,3,5,6tetrahydro-1,4-thiazine-3-carboxylate (8.8 g) and triethylamine (10.1 g) in chloroform (125 cc). The solution obtained is stirred for 3 hours at a temperature of the order of 20° C. and triethylamine (10.1 g) is then added, followed in the course of 15 minutes, at a temperature of between 24° C. and 36° C., by nicotinoyl chloride hydrochloride (8.9 g). The solution obtained is stirred for 16 hours at a temperature of the order of 20° C. and then for 2 hours at the boil. The reaction mixture is cooled to a temperature of the order of 20° C. and treated with a mixture of chloroform (250 cc) and distilled water (100 cc). The organic phase is separated off by decantation, washed with distilled water (100 cc) and then twice with a 2N aqueous solution of sodium hydroxide (300 cc in total) and twice with distilled water (200 cc in total), dried over anhydrous potassium carbonate, treated with decolourising charcoal (0.5 g) and filtered, and the filtrate is concentrated to dryness under reduced pressure (20 mm Hg; 2.7 kPa) at a temperature of the order of 60° C. This gives a crude product (17.5 g). This product is chromatographed on a column of diameter 6 cm, containing silica (0.04–0.063 mm) (480 g). Elution is carried out with a mixture of ethyl acetate and methanol (98/2 by volume) under a pressure of 0.5 bar (51 kPa), 100 cc fractions being collected. The first 14 fractions are discarded; the next 9 fractions are combined and concentrated to dryness under reduced pressure (20 mm Hg; 2.7 kPa) at a temperature of the order of 60° C. This gives ethyl N-nicotinoyl-2,3,5,6tetrahydro-1,4-thiazine-3-carboxylate (9.6 g) in the form of a yellow oil.

[Rf=0.35; chromatography on a thin layer of silica gel; solvent: ethyl acetate/methanol (98/2 by volume)].

The ethyl 2,3,5,6-tetrahydro 1,4-thiazine-3-carboxylate can be obtained according to B. BELLEAU, J. Med. Pharm. Chem. 2, 553 (1960).

EXAMPLE 10

A suspension of N-nicotinoyl-3,4,5,6-tetrahydro-2H-1,3-thiazine-4-carboxylic acid (34.5 g)and 2-chloroacylonitrile (119 g) in acetic anhydride (600 cc) is heated for 3 hours 30 minutes at a temperature of the order of 95° C. The solution obtained is cooled at a temperature of the order of 4° C. for 1 hour, with stirring. The crystals which have appeared are filtered off, washed twice with acetic anhydride cooled to a temperature of the order of 4° C. (10 cc in total) and twice with isopropyl ether (30 cc in total) and then dried under reduced pressure (20 mm Hg; 2.7 kPa) at a temperature of the order of 20° C., in the presence of potassium hydroxide pellets. This gives 6-(pyridin-3-yl)-1,2-dihydro-4H-pyrrolo[ 1,2-c]-1,3-thiazine-8-carbonitrile as the hydrochloride (16.4 g) in the form of ochre crystals melting at 195° C.

A solution of 6-(pyridin-3-yl)-1,2-dihydro-4H-pyrrolo[1,2-c]-1,3-thiazine-8-carbonitrile hydrochloride (0.8 g) in distilled water (25 cc) is brought to a pH of the order of 10 by adding an N aqueous solution of sodium hydroxide and extracted 3 times with ethyl acetate (100 cc in total). The organic extracts are combined, washed 3 times with distilled water (90 cc in total, dried over anhydrous magnesium sulphate, treated with decolourising charcoal (0.1 g) and filtered, and the filtrate is concentrated to dryness under reduced pressure (20 mm Hg; 2.7 kPa) at a temperature of the order of 50° C. This gives 6-(pyridin-3-yl)-1,2-dihydro-4H-pyrrolo[1,2-c]1,3-thiazine-8-carbonitrile (0.5 g) in the form of ochre crystals melting at 156° C.

The N-nicotinoyl-3,4,5,6-tetrahydro-2H-1,3-thiazine -4-carboxylic acid can be prepared in the following manner:

A solution of ethyl N-nicotinoyl-3,4,5,6-tetrahydro-2H-1,3-thiazine-4-carboxylate (37.8 g) in a mixture of a 5 N aqueous solution of sodium hydroxide (80 cc) and ethanol (80 cc) is stirred at a temperature of the order of 20° C. for 16 hours. The solvent is then evaporated off under reduced pressure (20 mm Hg; 2.7 kPa) at a temperature of the order of 50° C. The residue is dissolved in distilled water (100 cc) and purified by passing the solution obtained over DOWEX 50WX-2 resin (50–100 mesh) (630 g) contained in a column of diameter 4.5 cm. Elution is carried out with distilled water (4000 cc), then with a mixture of water and methanol (50/50 by volume) (1000 cc), then with methanol (2000 cc) and then with distilled water (2000 cc). All the corresponding fractions are discarded. The next 6 fractions, each of 1000 cc, from elution with a 2% strength (v/v) aqueous solution of pyridine are combined and concentrated to dryness under reduced pressure (20 mm Hg; 2.7 kPa) at a temperature of the order of 50° C. The residue is taken up in ethanol (150 cc) and the solvent is evaporated off under reduced pressure (20 mm Hg; 2.7 kPa) at a temperature of the order of 50° C.; this operation is repeated once. The residue finally collected is dissolved in a boiling mixture of ethanol and water (60/40 by volume) (350 cc). The solution obtained is treated with decolourising charcoal (0.5 g) and filtered hot; the filtrate is cooled at a temperature of the order of 4° C. for 1 hour. The crystals which have appeared are filtered off, washed 3 times with a mixture of ethanol and water (60/40 by volume) (60 cc in total) and then 3 times with ethanol (60 cc in total) and dried under reduced pressure (20 mm Hg; 2.7 kPa) at a temperature of the order of 20° C., in the presence of potassium hydroxide pellets. This gives N-nicotinoyl-3,4,5,6-tetrahydro-2H-1,3-thiazine-4-carboxylic acid (24.2 g) in the form of white crystals melting at 214° C.

The ethyl N-nicotinoyl-3,4,5,6-tetrahydro-2H-1,3-thiazine-4-carboxylate can be prepared in the following manner:

A mixture of triethylamine (75 g) and chloroform (100 cc) is added in the course of 15 minutes, at a temperature of the order of 20° C., to a suspension of ethyl 3,4,5,6-tetrahydro-2H-1,3-thiazine-4-carboxylate hydrochloride (37.2 g) in chloroform (350 cc). Nicotinoyl chloride hydrochloride (50.4 g) is added to the solution thus obtained in the course of 10 minutes, at a temperature of the order of 20° C. The reaction mixture is heated at a temperature of the order of 65° C. for 1 hour 45 minutes and is then stirred at a temperature of the order of 20° C. for 16 hours. The reaction mixture is washed 3 times with distilled water (600 cc in total) and then 3 times with a saturated aqueous solution of potassium bicarbonate (600 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a product (52 g). This product is chromatographed on a column of diameter 5.2 cm, containing silica (0.063-0.2 mm) (520 g), 500 cc fractions being collected. The first fraction from elution with a mixture of cyclohexane and ethyl acetate (50/50 by volume) is discarded. The next 3 fractions from elution with a mixture of ethyl acetate and cyclohexane (50/50 by volume), the next two fractions from elution with a mixture of ethyl acetate and cyclohexane (70/30 by volume) and the next fraction from elution with a mixture of ethyl acetate and cyclohexane (80/20 by volume) are combined and concentrated to dryness under reduced pressure (20 mm Hg; 2.7 kPa) at a temperature of the order of 50° C. This gives ethyl N-nicotinoyl-3,4,5,6-tetrahydro-2H-1,3-thiazine-4-carboxylate (37.8 g) in the form of a yellow oil. [Rf=0.33; chromatography on a thin layer of silica gel; solvent: ethyl acetate/cyclohexane (80/20 by volume)].

The ethyl 3,4,5,6-tetrahydro-2H-1,3-thiazine-4-carboxylate hydrochloride can be prepared in the following manner:

A suspension of 3,4,5,6-tetrahydro-2H-1,3-thiazine-4-carboxylic acid (47.7 g) in ethanol (650 cc) is saturated with a stream of dry hydrogen chloride for 4 hours at a temperature of the order of 20° C. The suspension is stirred for 3 days at a temperature of the order of 20° C. and is then heated at a temperature of the order of 80° C. for 3 hours 20 minutes, with stirring. After the solution obtained has cooled to a temperature of the order of 4° C., the crystals which have appeared are filtered off, washed 3 times with ethanol cooled to a temperature of the order of 4° C. (30 cc in total) and then 3 times with diethyl ether (120 cc in total) and dried under reduced pressure (20 mm Hg; 2.7 kPa) at a temperature of the order of 20° C., in the presence of potassium hydroxide pellets. This gives ethyl 3,4,5,6-tetrahydro-2H-1,3-thiazine-4-carboxylate hydrochloride (37.2 g) in the form of white crystals melting at 185° C.

The 3,4,5,6-tetrahydro-2H-1,3-thiazine-4-carboxylic acid can be prepared according to J. C. WRISTON, Jr. and C. G. MACKENZIE, J. Biol. Chem., 225, 607 (1957).

EXAMPLE 11

A mixture of 5-(pyridin-3-yl)-1H,3H-pyrrolo[1,2-c]thiazole-7-carbonitrile (18.7 g), potassium hydroxide pellets (16.3 g) and ethylene glycol (160 cc) is heated at a temperature of the order of 155° C. for 2 hours, with stirring. After stirring for 16 hours at a temperature of the order of 20° C., the solvent is evaporated off under reduced pressure (2 mm Hg; 0.27 kPa) at a temperature of the order of 100° C. The residue is dissolved in distilled water (100 cc) and the solution obtained is brought to a pH of the order of 5 by adding a 2N aqueous solution of hydrochloric acid. The crystals which have appeared are filtered off, washed 3 times with distilled water (150 cc in total) and then 3 times with acetone (150 cc in total) and dried under reduced pressure (20 mm Hg; 2.7 kPa) at a temperature of the order of 20° C., in the presence of potassium hydroxide pellets. This gives a crude product (17.7 g) melting at 264° C. This product is combined with a product prepared in the same way in a previous operation (1.3 g) and dissolved in a mixture of butan-1-ol (650 cc) and dimethylformamide (150 cc), heated beforehand to a temperature of the order of 115° C. Decolourising charcoal (0.5 g) is added to the solution obtained and the mixture is filtered hot. The filtrate is cooled at a temperature of the order of 4° C. for 16 hours. The crystals which have appeared are filtered off, washed twice with dimethylformamide (50 cc in total), 3 times with ethanol (150 cc in total), 3 times with isopropyl ether (150 cc in total) and then 3 times with diethyl ether (150 cc in total) and dried under reduced pressure (20 mm Hg; 2.7 kPa) at a temperature of the order of 20° C., in the presence of potassium hydroxide pellets. This gives a product (16.1 g) melting at 266° C. This product is suspended in distilled water (250 cc) and the suspension is stirred at a temperature of the order of 20° C. for 2 hours. The crystals are filtered off, washed 5 times with distilled water (150 cc in total), 3 times with ethanol (90 cc in total), 3 times with isopropyl ether (90 cc in total) and then 3 times with diethyl ether (90 cc in total) and dried under reduced pressure (20 mm Hg; 2.7 kPa) at a temperature of the order of 100° C., in the presence of potassium hydroxide pellets. This gives 5-(pyridin-3-yl)-1H,3H-pyrrolo[1,2-c]thiazole-7-carboxylic acid (15.5 g) in the form of cream crystals melting at 266° C.

The 5-(pyridin-3-yl)-1H,3H-pyrrolo[1,2-c]thiazole-7-carbonitrile is prepared as in Example 3.

EXAMPLE 12

A suspension of 5-(pyridin-3-yl)-1H,3H-pyrrolo[1,2-c]thiazole-7-carbothioamide (81.3 g) and methyl iodide (49 g) in a mixture of acetone (3,110 cc) and dimethylformamide (1,550 cc) is stirred at a temperature of the order of 20° C. for 3 days. The crystals which have appeared are filtered off, washed 3 times with acetone (1,500 cc in total) and then twice with diethyl ether (500 cc in total) and dried under reduced pressure (20 mm Hg; 2.7 kPa) at a temperature of the order of 20° C., in the presence of potassium hydroxide pellets. This gives S-methyl 5-(pyridin-3-yl)-1H,3H-pyrrolo[1,2-c]thiazole-7-thiocarboximidate hydroiodide (113 g) in the form of yellow crystals melting at 262° C.

The 5-(pyridin-3-yl)-1H,3H-pyrrolo-[1,2-c]thiazole-7-carbothioamide can be prepared in the following manner:

A suspension of 5-(pyridin-3-yl)-1H,3H-pyrrolo[1,2-c]thiazole-7-carbonitrile (22.7 g) in a mixture of triethylamine (14 cc) and pyridine (32 cc) is saturated for 5 hours, at a temperature of the order of 20° C., with a gaseous stream of hydrogen sulphide. After stirring at a temperature of the order of 20° C. for 3 days, pyridine (32 cc) is added to the reaction mixture, the suspension is saturated again for 8 hours, at a temperature of the order of 20° C., with a gaseous stream of hydrogen sulphide and the stirring is then continued for 16 hours at a temperature of the order of 20° C. The same operation is repeated twice. The suspension is saturated again for a further 3 hours, at a temperature of the order of 20° C., with a gaseous stream of hydrogen sulphide and the reaction mixture is then poured into distilled water (500 cc). The crystals which have appeared are filtered off, washed 4 times with distilled water (200 cc in total), then twice with ethanol (100 cc in total) and then twice with isopropyl ether (100 cc in total) and dried under reduced pressure (20 mm Hg; 2.7 kPa) at a temperature of the order of 20° C., in the presence of potassium hydroxide pellets. This gives a crude product (26 g) melting at 230° C. This product is dissolved in dimethylformamide (250 cc) at a temperature of the order of 100° C. The solution obtained is treated with decolourising charcoal (1 g) and filtered hot; the filtrate is cooled at a temperature of the order 4° C. for 2 hours. The crystals which have appeared are filtered off, washed twice with dimethylformamide (40 cc in total), 3 times with ethanol (150 cc in total) and then 3 times with isopropyl ether (150 cc in total) and dried under reduced pressure (20 mm Hg; 2.7 kPa) at a temperature of the order of 20° C., in the presence of potassium hydroxide pellets. This gives 5-(pyridin-3-yl)-1H,3H-pyrrolo[1,2-c]thiazole-7-carbothioamide (21 g) in the form of yellow crystals melting at 243° C.

The 5-(pyridin-3-yl)-1H,3H-pyrrolo[1,2-c]thiazole-7-carbonitrile is prepared as described in Example 3.

APPLICATION EXAMPLE 1

A solution of 2-diethylaminoethylamine (9.5 g) in anhydrous tetrahydrofuran (50 cc) is added in the course of 10 minutes, at a temperature of the order of 25° C., to a solution of 3-(pyridin-3-yl)-1H,3H-pyrrolo[1,2-c]thiazole-7-carboxylic acid (10.2 g) and N,N'-carbonyldiimidazole (10.1 g) in anhydrous tetrahydrofuran (150 cc), stirred under dry nitrogen at a temperature of the order of 20° C. for 1 hour 20 minutes. After stirring for one hour at a temperature of the order of 20° C., the solvent is evaporated off under reduced pressure (20 mm Hg; 2.7 kPa) at a temperature of the order of 40° C. The residue obtained is taken up in distilled water (700 cc) and the mixture is extracted 5 times with ethyl acetate (750 cc in total). The organic extracts are combined, washed 5 times with distilled water (500 cc) in total, dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 40° C. This gives a crude product (12.4 g). This product, combined with the product prepared in the same manner in another earlier operation (2 g) is dissolved in a boiling mixture of cyclohexane and ethyl acetate (50/50 by volume) (100 cc). The solution obtained is treated with decolourising charcoal (0.5 g) and then filtered hot; the filtrate is cooled at a temperature of the order of 4° C. for 2 hours. The crystals which have appeared are filtered off, washed 3 times with isopropyl ether (45 cc in total) and dried under reduced pressure (20 mm Hg; 2.7 kPa) at a temperature of the order of 20° C., in the presence of potassium hydroxide pellets. This gives N-(2-diethylaminoethyl)-3-(pyridin-3-yl)-1H,3H-pyrrolo[1,2-c]thiazole-7-carboxamide (9.8 g) in the form of white crystals melting at 129° C.

The 3-(pyridin-3-yl)-1H,3H-pyrrolo-[1,2-c]thiazole-7-carboxylic acid can be obtained as in Example 1.

APPLICATION EXAMPLE 2

A solution of 3-(pyridin-3-yl)-1H,3H-pyrrolo[1,2-c]thiazole-7-carboxylic acid (2 g) and N,N'-carbonyldiimidazole (1.45 g) in anhydrous tetrahydrofuran (40 cc) is stirred at a temperature of the order of 20° C. for 4 hours. The solution obtained is treated with decolourising charcoal (0.5 g) and filtered, and the filtrate is concentrated to dryness under reduced pressure (20 mm Hg; 2.7 kPa) at a temperature of the order of 45° C. The residue is taken up in distilled water (100 cc) and the suspension obtained is stirred at a temperature of the order of 20° C. for 30 minutes. The crystals are filtered off, washed 3 times with distilled water (60 cc in total) and dried under reduced pressure (20 mm Hg; 2.7 kPa) at a temperature of the order of 20° C., in the presence of potassium hydroxide pellets. This gives a crude product (2 g). This product is dissolved in boiling isopropanol (35 cc). The solution obtained is cooled at a temperature of the order of 4° C. for 1 hour. The crystals which have appeared are filtered off, washed twice with isopropanol cooled to a temperature of the order of 4° C. (20 cc in total) and twice with isopropyl ether (20 cc in total) and then dried under reduced pressure (20 mm Hg; 2.7 kPa) at a temperature of the order of 20° C., in the presence of potassium hydroxide pellets. This gives 7-(imidazol-1-yl-carbonyl)-3-(pyridin-3-yl)-1H,3H-pyrrolo[1,2-c]thiazole (1.7 g) in the form of cream crystals melting at 117° C.

The 3-(pyridin-3-yl)-1H,3H-pyrrolo[1,2-c]thiazole-7-carboxylic acid is prepared as in Example 1.

APPLICATION EXAMPLE 3

A solution of 7-(imidazol-1-yl-carbonyl)-3-(pyridin-3-yl)-1H,3H-pyrrolo[1,2-c]thiazole (16 g) and 2-aminopyridine (10.2 g) in anhydrous dimethylformamide (150 cc) is heated for 5 hours 30 minutes at a temperature of the order of 150° C. The solution is then concentrated to dryness under reduced pressure (20 mm Hg; 2.7 kPa) at a temperature of the order of 80° C. and the residual oil is taken up in distilled water (500 cc). Crystals appear. The suspension is stirred at a temperature of the order. of 20° C. for 16 hours. The crystals are filtered off, washed 3 times with distilled water (300 cc in total) and dried under reduced pressure (20 mm Hg; 2.7 kPa) at a temperature of the order of 20° C., in the presence of potassium hydroxide pellets. This gives a crude product (14.6 g) melting at 141° C. This product is dissolved in boiling ethanol (75 cc). The solution obtained is treated with decolourising charcoal (0.5 g) and filtered hot. The filtrate is cooled at a temperature of the order of 4° C. for 1 hour. The crystals which have appeared are filtered off, washed twice with ethanol cooled to a temperature of the order of 4° C. (10 cc in total) and 3 times with diethyl ether (15 cc in total) and then dried under reduced pressure (20 mm Hg; 2.7 kPa) at a temperature of the order of 20° C., in the presence of potassium hydroxide pellets. This gives N-(pyridin-2-yl)-3-(pyridin-3-yl)-1H,3H-pyrrolo[1,2-c]thiazole-7-carboxamide (11.6 g) in the form of beige crystals melting at 145° C.

The 7-(imidazol-1-yl-carbonyl)-3-(pyridin-3-yl)-1H,3H-pyrrolo[1,2-c]thiazole is prepared as in Application Example 2.

APPLICATION EXAMPLE 4

Triethylamine (5.1 g) is added to a solution of the ethoxymagnesium derivative of diethyl malonate in a mixture of ether and ethanol (3/1 by volume) (65 cc), prepared from magnesium (1.34 g) and diethyl malonate (8.8 g); 7-chloroformyl-3-(pyridin-3-yl)-1H,3H-pyrrolo[1,2-c]thiazole hydrochloride (15 g) is added to the suspension obtained in the course of 15 minutes, at a temperature of between 25° C. and 30° C., and the mixture is then diluted with anhydrous tetrahydrofuran (35 cc) and stirred at a temperature of the order of 20° C. for 16 hours. The reaction mixture is then taken up in a 2 N aqeuous solution of hydrochloric acid (25 cc) and extracted 5 times with ethyl acetate (750 cc in total). The organic extracts are combined, washed 5 times with distilled water (250 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a product (19 g) melting at 110° C. This product is dissolved in a mixture of acetic acid (25 cc), distilled water (15 cc) and concentrated sulphuric acid (3 cc). The solution obtained is heated at a temperature of the order of 100° C. for 9 hours 30 minutes and is then cooled to a temperature of the order of 20° C., diluted with distilled water (150 cc), treated with decolourising charcoal (0.5 g) and filtered, and the filtrate is brought to a pH of the order of 9 by adding sodium carbonate and extracting 3 times with ethyl acetate (450 cc in total). The organic extracts are combined, washed 3 times with distilled water (450 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 45° C. This gives a product (9.5 g). This product is chromatographed on a column of diameter 6 cm, containing silica (0.04–0.063 mm) (480 g), elution being carried out with mixtures of cyclohexane and ethyl acetate under a pressure of 0.5 bar (51 kPa) and 200 cc fractions being collected. The first 9 fractions from elution with a mixture of ethyl acetate and cyclohexane (80/20 by volume) are discarded. The next 9 fractions from elution with a mixture of ethyl acetate and cyclohexane (85/15 by volume) are combined and concentrated to dryness under reduced pressure (20 mm Hg; 2.7 kPa) at a temperature of the order of 50° C. This gives a product (7.2 g). This product is dissolved in boiling isopropanol (30 cc). The solution obtained is treated with decolourising charcoal (0.5 g) and filtered hot. The filtrate is cooled at a temperature of the order of 4° C. for 1 hour. The crystals which have appeared are filtered off, washed 3 times with isopropanol cooled to a temperature of the order of 4° C. (15 cc in total) and dried under reduced pressure (20 mm Hg; 2.7 kPa) at a temperature of the order of 20° C., in the presence of potassium hydroxide pellets. This gives 7-acetyl-3-(pyridin-3-yl)-1H,3H-pyrrolo[1,2-c]thiazole (5.7 g) in the form of cream crystals melting at 100° C.

The 7-chloroformyl-3-(pyridin-3-yl)-1H,3H-pyrrolo[1,2-c]thiazole hydrochloride is prepared in the following manner:

A suspension of 3-(pyridin-3-yl)-1H,3H-pyrrolo[1,2-c]thiazole-7-carboxylic acid (9.8 g) in a mixture of thionyl chloride (23.8 g), dimethylformamide (0.1 cc) and 1,2-dichloroethane (100 cc) is heated at the boil for 1 hour 15 minutes. After the reaction mixture has cooled, the solvent is evaporated off under reduced pressure (20 mm Hg; 2.7 kPa) at a temperature of the order of 50° C. The residue obtained is suspended in anhydrous cyclohexane (100 cc) and the crystals are filtered off, washed twice with anhydrous cyclohexane (10 cc in total) and dried under reduced pressure (20 mm Hg; 2.7 kPa) at a temperature of the order of 20° C. This gives 7-chloroformyl-3-(pyridin-3-yl)-1H,3H-pyrrolo[1,2-c]thiazole-7-hydrochloride (12.1 g) in the form of ochre crystals melting at 185° C.

The 3-(pyridin-3-yl)-1H,3H-pyrrolo[-1,2-c-thiazole-7-carboxylic acid is prepared as in Example 1.

The ethoxymagnesium derivative of diethyl malonate is prepared according to G. A. REYNOLDS and C. R. HAUSER, Org. Synth. Coll. Vol. 4,708 (1963).

APPLICATION EXAMPLE 5

A suspension of S-methyl 3-(pyridin-3-yl)-1H,3H-pyrrolo[1,2-c]thiazole-7-thiocarboximidate hydroiodide (9.5 g) and N,N-dimethylhydrazine (1.6 g) in ethanol (125 cc) is heated at a temperature of the order of 78° C. for 4 hours 30 minutes. The solution obtained is concentrated to dryness under reduced pressure (20 mm Hg; 2.7 kPa) at a temperature of the order of 60° C. The residue obtained is dissolved in distilled water (250 cc) and the resulting solution is extracted 3 times with ethyl acetate (300 cc in total), treated with decolourising charcoal (0.5 g) and filtered, and the filtrate is brought to a pH of the order of 10 by adding a 10 N aqueous solution of sodium hydroxide and extracted 3 times with ethyl acetate (300 cc in total). The organic extracts are combined, washed 3 times with distilled water (300 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a crude product (4.8 g), which is chromatographed on a column of diameter 4 cm, containing silica (0.04–0.063 mm) (320 g). Elution is carried out under a pressure of 0.5 bar (51 kPa) with mixtures of methylene chloride and methanol, 100 cc fractions being collected. The first 13 fractions from elution with a mixture of methylene chloride and methanol (90/10 by volume) are discarded. The next 4 fractions from elution with a mixture of methylene chloride and methanol (90/10 by Volume), the next 9 fractions from elution with a mixture of methylene chloride and methanol (80/20 by volume) and the next 10 fractions from elution with a mixture of methylene chloride and methanol (50/50 by volume) are combined and concentrated to dryness under reduced pressure (20 mm Hg; 2.7 kPa) at a temperature of the order of 60° C. This gives a product (3.1 g), which is dissolved in ethanol (20 cc). The turbid solution obtained is filtered and the filtrate is treated with a 5.35 N ethanolic solution of hydrogen chloride (8.1 cc); the hydrochloride obtained is precipitated from it solution by adding diethyl ether (2 cc). After cooling at a temperature of the the order 4° C. for 16 hours, the crystals are filtered off, washed 5 times with a mixture of diethyl ether and ethanol (50/50 by volume) (75 cc in total) and 5 times with diethyl ether (75 cc in total) and then dried under reduced pressure (20 mm Hg; 2.7 kPa) at a temperature of the order of 20° C., in the presence of potassium hydroxide pellets. This gives 3-(pyridin-3-yl)-1H,3H-pyrrolo[1,2-c]thiazole-7-carboxamide-dimethylhydrazone hydrochloride (2.7 g) in the form of cream crystals melting at 195° C.

The S-methyl 3-(pyridin-3-yl)-1H,3H-pyrrolo[1,2-c]thiazole-7-thiocarboximidate hydroiodide can be prepared as in Example 2.

APPLICATION EXAMPLE 6

A suspension of 5-(pyridin-3-yl)-1H,3H-pyrrolo[1,2-c]thiazole-7-carbonitrile (11.35 g) and powdered potassium hydroxide (14 g) in tert.-butyl alcohol (100 cc) is heated at 85° C. for 1 hour. After stirring for 16 hours at a temperature of the order of 20° C., the reaction mixture is poured into distilled water (2 litres). The suspension is stirred at a temperature of the order of 20° C. for 15 minutes and the crystals which have appeared are then filtered off, washed 8 times with distilled water (1,200 cc in total) and then 3 times with ethanol (150 cc in total) and dried under reduced pressure (20 mm Hg; 2.7 kPa) at a temperature of the order of 20° C., in the presence of potassium hydroxide pellets. This gives a crude product (10.5 g), which is combined with a product prepared in the same way in an earlier operation (3.9 g) and dissolved in boiling ethanol (850 cc). The solution is treated with decolourising charcoal (0.5 g) and filtered hot. The filtrate is cooled at a temperature of the order of 4° C. for 3 days. The crystals which have appeared are filtered off, washed 3 times with ethanol cooled to a temperature of the order of 4° C. (30 cc in total) and dried under reduced pressure (20 mm Hg; 2.7 kPa) at a temperature of the order of 20° C., in the presence of potassium hydroxide pellets. This gives 5-(pyridin-3-yl)-1H,3H-pyrrolo[1,2-c]thiazole-7-carboxamide (11.3 g) in the form of cream crystals melting at 215° C.

The 5-(pyridin-3-yl)-1H,3H-pyrrolo[1,2-c]thiazole-7-carbonitrile is prepared as described in Example 3.

APPLICATION EXAMPLE 7

A suspension of 5-(pyridin-3-yl)-1H,3H-pyrrolo[1,2-c]thiazole-7-carbonitrile (22.7 g) in a mixture of triethylamine (14 cc) and pyridine (32 cc) is saturated for 5 hours, at a temperature of the order of 20° C., with a gaseous stream of hydrogen sulphide. After stirring at a temperature of the order of 20° C. for 3 days, pyridine (32 cc) is added to the reaction mixture, the suspension is saturated again for 8 hours, at a temperature of the order of 20° C., with a gaseous stream of hydrogen sulphide and the stirring is then continued for 16 hours at a temperature of the order of 20° C. The same operation is repeated twice. The suspension is saturated again for a further 3 hours, at a temperature of the order of 20° C., with a gaseous stream of hydrogen sulphide and the reaction mixture is then poured into distilled water (500 cc). The crystals which have appeared are filtered off, washed 4 times with distilled water (200 cc in total), then twice with ethanol (100 cc in total) and then twice with isopropyl ether (100 cc in total) and dried under reduced pressure (20 mm Hg; 2.7 kPa) at a temperature of the order of 20° C., in the presence of potassium hydroxide pellets. This gives a crude product (26 g) melting at 230° C. This product is dissolved in dimethylformamide (250 cc) at a temperature of the order of 100° C. The solution obtained is treated with decolourising charcoal (1 g) and filtered hot; the filtrate is cooled at a temperature of the order 4° C. for 2 hours. The crystals which have appeared are filtered off, washed twice with dimethylformamide (40 cc in total), 3 times with ethanol (150 cc in total) and then 3 times with isopropyl ether (150 cc in total) and dried under reduced pressure (20 mm Hg; 2.7 kPa) at a temperature of the order of 20° C., in the presence of potassium hydroxide pellets. This gives 5-(pyridin-3-yl)-1H,3H-pyrrolo[1,2-c]thiazole-7-carbothioamide (21 g) in the form of yellow crystals melting at 243° C.

The 5-(pyridin-3-yl)-1H,3H-pyrrolo[1,2-c]thiazole-7-carbonitrile is prepared as described in Example 3.

APPLICATION EXAMPLE 8

A suspension of 5-(pyridin-3-yl)-2,3-dihydro-1H-pyrrolizine-7-carbonitrile (14.6 g) and powdered potassium hydroxide (23.1 g) in tert.-butyl alcohol (140 cc) is heated at 82° C. for 2 hours. During this period, the mixture is seen to pass through a clear homogeneous phase after 10 minutes, this being followed by precipitation 20 minutes later. After cooling to a temperature of the order of 20° C., the solvent is evaporated off under reduced pressure (20 mm Hg; 2.7 kPa) at a temperature of the order of 60° C. The crystalline residue obtained is suspended in distilled water (250 cc) and the suspension is stirred at a temperature of the order of 20° C. for 30 minutes. The crystals are filtered off, washed 4 times with distilled water (200 cc in total) and then 3 times with isopropyl ether (150 cc in total) and dried reduced pressure (20 mm Hg; 2.7 kPa) at a temperature of the order of 20° C., in the presence of potassium hydroxide pellets. This gives a crude product (15.5 g) melting at 206° C. This product is dissolved in boiling ethanol (150 cc). The solution obtained is treated with decolourising charcoal (0.5 g) and filtered; the filtrate is cooled at a temperature of the order of 10° C. or 2 hours. The crystals are filtered off and dried under reduced pressure (20 mm Hg; 2.7 kPa) at a temperature of the order of 20° C., in the presence of potassium hydroxide pellets. This gives 5-(pyridin-3-yl)-2,3-dihydro-1H-pyrrolizine-7-carboxamide (9.6 g) in the form of cream crystals melting at 210° C.

The 5-(pyridin-3-yl)-2,3-dihydro-1H-pyrrolizine-7-carbonitrile can be prepared as in Example 4.

APPLICATION EXAMPLE 9

A solution of 2-diethylaminoethylamine (13.9 g) in methylene chloride (50 cc) is added in the course of 20 minutes, at a temperature of the order of 20° C., to a suspension of 7-chloroformyl-5-(pyridin-3-yl)-1H,3H-pyrrolo[1,2-c]thiazole hydrochloride (12 g) in methylene chloride (200 cc). The solution obtained is stirred for 16 hours at a temperature of the order of 20° C. A product precipitates. Methylene chloride (250 cc) and a 2N aqueous solution of sodium hydroxide (100 cc) are then added; the organic phase is separated off by decantation, washed with a 2N aqueous solution of sodium hydroxide (100 cc) and then 3 times with distilled water (600 cc in total), dried over anhydrous potassium carbonate, treated with decolourising charcoal (0.5 g) and filtered, and the filtrate is concentrated to dryness under reduced pressure (20 mm Hg; 2.7 kPa) at a temperature of the order of 60° C. This gives a crude product (12 g). This product is dissolved in boiling acetonitrile (60 cc). The solution obtained is treated with decolourising charcoal (0.5 g) and filtered hot; the filtrate is cooled at a temperature of the order of 4° C. for 2 hours. The crystals which have appeared are filtered off, washed twice with acetonitrile cooled to a temperature of the order of 4° C. (20 cc in total) and then 3 times with isopropyl ether (150 cc in total) and dried under reduced pressure (20 mm Hg; 2.7 kPa) at a temperature of the order of 20° C., in the presence of potassium hydroxide pellets. This gives N-(2-diethylaminoethyl)-5-(pyridin-3-yl) -1H,3H-pyrrolo[1,2-c]thiazole-7-carboxamide (6.4 g) in the form of light beige crystals melting at 106° C.

The 7-chloroformyl-5-(pyridin-3-yl)-1H,3H-pyrrolo[1, 2-c]thiazole hydrochloride is prepared in the following manner:

A suspension of 5-(pyridin-3-yl)-1H,3H-pyrrolo 1,2-c]thiazole-7-carboxylic acid (8.8 g) in a mixture of thionyl chloride (6.25 cc), dimethylformamide (0.05 cc) and 1,2-dichloroethane (100 cc) is heated under reflux for 2 hours 30 minutes, with stirring. The reaction mixture is cooled to a temperature of the order of 20° C. and concentrated to dryness under reduced pressure (20 mm Hg; 2.7 kPa) at a temperature of the order of 60° C. The residue obtained is suspended in cyclohexane (150 cc) and the solvent is evaporated off under reduced pressure (20 mm Hg; 2.7 kPa) at a temperature of the order of 60° C. The same operation is repeated twice. This gives 7-chloroformyl-5-(pyridin-3-yl)-pyrrolo[1,2-c]thiazole hydrochloride (10 g) in the form of cream crystals melting at 220° C.

The 5-(pyridin-3-yl)-1H,3H-pyrrolo [1,2-c]thiazole -7-carboxylic acid can be prepared as described in Example 11.

APPLICATION EXAMPLE 10

A suspension of S-methyl 5-(pyridin-3-yl)-1H,3H-pyrrolo[1,2-c]thiazole-7-thiocarboximidate hydroiodide (20.2 g) and N,N-dimethylhydrazine (3.4 g) in ethanol (100 cc) is heated at the boil for 5 hours 30 minutes and then filtered hot. After cooling to a temperature of the order of 20° C., diethyl ether (350 cc) is added to the filtrate. The suspension obtained is stirred at a temperature of the order of 20° C. for 30 minutes. The crystals which have appeared are filtered off, washed twice with a mixture of ethanol and diethyl ether (50/50 by volume) (100 cc in total) and dried under reduced pressure (20 mm Hg; 2.7 kPa) at a temperature of the order of 20° C., in the presence of potassium hydroxide pellets. The product obtained is suspended in a mixture of water (300 cc) and ethyl acetate (300 cc). A 10N aqueous solution of sodium hydroxide (100 cc) is added to this suspension. The organic phase is separated off by decantation and the aqueous phase is extracted twice with ethyl acetate (300 cc in total). The organic extracts are combined, washed 3 times with distilled water (300 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 50° C. This gives a crude product (9.3 g) melting at 168° C. This product is dissolved in boiling ethanol (100 cc). The solution obtained is treated with decolourising charcoal (0.5 g) and filtered hot; the filtrate is cooled at a temperature of the order of 4° C. for 1 hour. The crystals which have appeared are filtered off, washed 3 times with ethanol cooled to a temperature of the order of 4° C. (30 cc in total) and 3 times with isopropyl ether (60 cc in total) and dried under reduced pressure (20 mm Hg; 2.7 kPa) at a temperature of the order of 20° C., in the presence of potassium hydroxide pellets. This gives 5-(pyridin-3-yl)-1H,3H-pyrrolo[1,2-c]thiazole-7-carboxamide-dimethylhydrazone (4.95 g) in the form of cream crystals melting at 170° C.

The S-methyl 5-(pyridin-3-yl)-1H,3H-pyrrolo[1, 2-c]thiazole-7-carboximidate hydroiodide is prepared as in Example 12.

APPLICATION EXAMPLE 11

A suspension of S-methyl 5-(pyridin-3-yl)-1H,3H-pyrrolo[1, 2-c]thiazole-7-thiocarboximidate hydroiodide (20.2 g), piperidine (8.6 g) and acetic acid (10.5 g) in chloroform (500 cc) is stirred at 20° C. for 3 days. A 2.8 N aqueous solution of sodium hydroxide (360 cc) and chloroform (200 cc) are then added to the suspension. The organic phase is separated off by decantation and the aqueous phase is extracted twice with chloroform (1,000 cc in total). The organic extracts are combined, washed 3 times with distilled water (750 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a product (15 g), which is taken up in boiling ethyl acetate (200 cc). After cooling to a temperature of the order of 20° C., the crystals which have appeared are filtered off and the filtrate is concentrated to dryness under reduced pressure (20 mm Hg; 2.7 kPa) at a temperature of the order of 60° C. This gives a product (14.1 g). This product is dissolved in ethanol (130 cc) and the solution obtained is treated with a 4.7N ethanolic solution of hydrogen chloride (19.3 cc) and is then cooled at a temperature of the order of 4° C. for 1 hour. The crystals which have appeared are filtered off, washed 3 times with ethanol (75 cc in total) and 3 times with diethyl ether (150 cc in total) and dried under reduced pressure (20 mm Hg; 2.7 kPa) at a temperature of the order of 20° C., in the presence of potassium hydroxide pellets. This gives a crude product (13.7 g) in the form of the dihydrochloride, melting at 264° C. This product is combined with a product prepared in a previous operation (2.4 g) and is dissolved in distilled water (200 cc). A 1N aqueous solution of sodium hydroxide (84 cc) and ethyl acetate (250 cc) are added to the solution obtained. The organic phase is separated off by decantation and the aqueous phase is extracted twice with ethyl acetate (200 cc in total). The organic extracts are combined, dried over anhydrous potassium carbonate, treated with decolourising charcoal (0.5 g) and filtered, and the filtrate is concentrated to dryness under reduced pressure (20 mm Hg; 2.7 kPa) at a temperature of the order of 60° C. This gives a product (13 g). This product is chromatographed on a column of diameter 2.4 cm, containing silica (0.063–0.2 mm) (65 g), elution being carried out with mixtures of acetonitrile and aqueous ammonia (d =0.92) and 100 cc fractions being collected. The first 2 fractions from elution with a mixture of acetonitrile and aqueous ammonia (95/5 by volume) are discarded. The third fraction from elution with a mixture of acetonitrile and aqueous ammonia (95/5 by volume) and the next 9 fractions from elution with a mixture of acetonitrile and aqueous ammonia (90/10 by volume) are combined and concentrated to dryness under reduced pressure (20 mm Hg; 2.7 kPa) at a temperature of the order of 40° C. This gives a product (11.3 g). This product is chromatographed again on a column of diameter 6 cm, containing silica (0.04–0.063 mm) (480 g). Elution is carried out with a mixture of methylene chloride, methanol and 20% strength aqueous ammonia (12/6/1 by volume) under a pressure of 0.5 bar (51 kPa), 100 cc fractions being collected. The first 7 fractions are discarded and the next 14 fractions are combined and concentrated to dryness under reduced pressure (20 mm Hg; 2.7 kPa) at a temperature of the order of 40° C. This gives a product (9.6 g). This product is taken up in boiling ethyl acetate (350 cc) and the suspension obtained is filtered hot; the filtrate is then cooled to a temperature of the order of 20° C. and concentrated to dryness under reduced pressure (20 mm Hg; 2.7 kPa) at a temperature of the order of 60° C. This gives a product (9.1 g). This product is dissolved in ethanol (100 cc). The solution obtained is treated with 4.7N ethanolic solution of hydrogen chloride (12.4 cc) and is cooled at a temperature of the order of 4° C. for 2 hours. The crystals which have appeared are filtered off, washed twice with ethanol cooled at a temperature of the order of 4° C. (50 cc in in total) and then 3 times with diethyl ether (150 cc in total) and dried under reduced pressure (20 mm Hg; 2.7 kPa) at a temperature of the order of 20° C., in the presence of potassium hydroxide pellets. This gives a product (9.7 g). This product is dissolved in a boiling mixture of ethanol (175 cc) and distilled water (10 cc). The solution obtained is treated with decolourising charcoal (0.5 g) and filtered hot; the filtrate is cooled at a temperature of the order of 4° C. for 3 hours. The crystals which have appeared are filtered off, washed 3 times with ethanol (30 cc in total) and 3 times with diethyl ether (75 cc in total) and dried under reduced pressure (20 mm Hg; 2.7 kPa) at a temperature of the order of 20° C., in the presence of potassium hydroxide pellets. This gives 7-piperidinocarbonimidoyl-5-(pyridin-3-yl)-1H,3H-pyrrolo[1,2-c]thiazole dihydrochloride (4.5 g) in the form of pale yellow crystals melting at 284° C.

The S-methyl 5-(pyridin-3-yl)-1H,3H-pyrrolo[1,2-c]thiazole-7-thiocarboximidate hydroiodide is prepared as in Example 12.

APPLICATION EXAMPLE 12

A suspension of 6-(pyridin-3-yl)-3,4-dihydro-1H-pyrrolo[2, 1-c]-1,4-thiazine-8-carbonitrile (4.9 g) and powdered potassium hydroxide (6.7 g) in tert.-butyl alcohol (50 cc) is heated at the boil for 1 hour 15 minutes. The solvent is then evaporated off under reduced pressure (20 mm Hg; 2.7 kPa) at a temperature of the order of 60° C. and the residue is then suspended in distilled water (150 cc). The crystals which have appeared are filtered off, washed 3 times with distilled water (150 cc in total) and dried under reduced pressure (20 mm Hg; 2.7 kPa) at a temperature of the order of 20° C. This gives a crude product (5.2 g) melting at 186° C. This product is combined with a product prepared in the same way in previous operations (4.5 g) and is dissolved in boiling ethanol (250 cc). The solution obtained is treated with decolourising charcoal (0.5 g) and then filtered hot; the filtrate is cooled at a temperature of the 4° C. for 2 hours. The crystals which have appeared are filtered off, washed twice with ethanol cooled to a temperature of the order of 4° C. (50 cc in total) and then 3 times with diethyl ether (75 cc in total) and dried under reduced pressure (20 mm Hg; 2.7 kPa) at a temperature of the order of 20° C., in the presence of potassium hydroxide pellets. This gives 6-(pyridin-3-yl)-3,4-dihydro-1H-pyr-rolo[2,1-c]-1,4-thiazine-8-carboxamide (7.1 g) in the form of yellow crystals melting at 192° C.

The 6-(pyridin-3-yl)-3,4-dihydro-1H-pyrrolo[2, 1]-1,4-thiazine-8-carbonitrile can be prepared as in Example 9.

APPLICATION EXAMPLE 13

By following the procedure of example 12, but using 6-(pyridin-3-yl)-1,2-dihydro-4H-pyrrolo1,2-c-1,3-thiazine-8-carbonitrile, prepared as described in Example 10) as the starting material, 6-(pyridin-3-yl)-1,2-dihydro-4H-pyrrolo[1, 2-c]-1,3-thiazine-8-carboxamide 7.1. g) in the obtained in the form of white crystals melting at 220° C.

APPLICATION EXAMPLE 14

A suspension of powdered potassium hydroxide (11.2 g) and a mixture (in the ratio 69/31) of 6-cyano and 7-cyano-5-[2-(pyridin-3-yl)-vinyl]-1H,3H-pyrrolo[1,2-c]thiazole (10.2 g) in tert.-butyl alcohol (110 cc) is heated under reflux for one hour. The solvent is then evaporated off under reduced pressure (20 mm Hg; 2.7 kPa) at a temperature of the order of 50° C. After the addition of distilled water (200 cc), the crystals which have appeared are filtered off, washed four times with distilled water (120 cc in total) and dried under reduced pressure (20 mm Hg; 2.7 kPa) at a temperature of the order of 20° C., in the presence of potassium hydroxide pellets. This gives a crude product (11 g). This product is chromatographed on a column of diameter of 3.2 cm, containing silica (0.063-0.2 mm) (110 g), 1,000 cc fractions being collected. The first fraction from elution with pure methylene chloride, the second fraction from elution with a mixture of methylene chloride and methanol (97.5/2.5 by volume), the third fraction from elution with a mixture of methylene chloride and methanol (95/5 by volume) and the fourth fraction from elution with a mixture of nethylene chloride and methanol (92.5/7.5 by volume) are discarded. The fifth fraction from elution with a mixture of methylene chloride and methanol (90/10 by volume) and the sixth fraction from elution with a mixture of methylene chloride and methanol (85/15 by volume) are combined and concentrated to dryness under reduced pressure (20 mm Hg; 2.7 kPa) at a temperature of the order of 40° C. This gives a product (3.7 g) melting at 180° C. This product is dissolved in boiling acetonitrile (700 cc). After cooling at a temperature of the order of 4° C. for one hour, the crystals which have appeared are filtered off and dried and reduced pressure (20 mm Hg; 2.7 kPa) at a temperature of the order of 20° C., in the presence of potassium hydroxide pellets. This gives a product (2.4 g), which is combined with a product prepared in the same way in a previous operation (0.9 g) and chromatographed on a column of diameter 2.8 cm, containing silica (0.063-0.2 mm) (35 g), 500 cc fractions being collected. The first two fractions from elution with pure methylene chloride and the next two from elution with a mixture of methylene chloride and methanol (97.5/2.5 by volume) are discarded. The fifth and sixth fractions from elution with a mixture of methylene chloride and methanol (95/5 by volume) and the seventh fraction from elution with a mixture of methylene chloride and methanol (90/10 by volume) are combined and concentrated to dryness under reduced pressure (20 mm Hg; 2.7 kPa) at a temperature of the order of 40° C. This gives a product (3.1 g), which is dissolved in boiling acetonitrile (900 cc). The solution is treated with decolourising charcoal (0.3 g) and filtered hot. After cooling at a temperature of the order of 4° C. for 2 hours, the crystals which have appeared are filtered off, washed twice with acetonitrile (60 cc in total) and dried under reduced pressure (20 mm Hg; 2.7 kPa) at a temperature of the order of 20° C., in the presence of potassium hydroxide pellets. This gives 5-[2-(pyridin-3-yl)-vinyl]-1H,3H-pyrrolo[1,2-c]thiazole-7-carboxamide (2.1 g) melting at 242° C.

The mixture (69/31) of 6-cyano and 7-cyano-5-[2-(pyridin-3-yl)-vinyl]-1H,3H-pyrrolo[1,2-c]thiazole can be prepared as described in Example 5.

APPLICATION EXAMPLE 15

A suspension of 5-(pyridin-3-yl)-1H,3H-pyrrolo[1,2-c]thiazole-7-carbonitrile (3.6 g), ethanolamine (3.8 g) and lithium chloride (0.1 g) is heated at a temperature of the order of 122° C. for 22 hours. Ethanolamine (1.9 g) and lithium chloride (0.1 g) are then added to the reaction mixture and heating is continued for a further 26 hours. After the reaction mixture has cooled to a temperature of the order of 20° C., solidification is observed. Ethanol (25 cc) is then added in order to break up the crystals. After stirring for 30 minutes at a temperature of the order of 20° C., the crystals are filtered off, washed twice with ethanol (10 cc in total) and 3 times with isopropyl ether (75 cc in total) and then dried under reduced pressure (20 mm Hg; 2.7 kPa) at a temperature of the order of 20° C., in the presence of potassium hydroxide pellets. This gives a crude product (3.1 g) melting at 150° C. This product is dissolved in boiling ethanol (40 cc). The solution obtained is treated with decolourising charcoal (0.5 g) and filtered hot. The filtrate is cooled at a temperature of the order of 4° C. for 1 hour. The crystals which have appeared are filtered off, washed twice with ethanol (10 cc in total) and 3 times with isopropyl ether (45 cc) in total and then dried under reduced pressure (20 mm Hg; 2.7 kPa) at a temperature of the order of 20° C., in the presence of potassium hydroxide pellets. This gives N-[2-(2-hydroxyethyl)-aminoethyl]-5-(pyridin-3-yl)-1H,3H-pyrrolo[1,2-c]thiazole-7-carboxamide (2 g) in the form of pale yellow crystals melting at 163° C.

The 5-(pyridin-3-yl)-1H,3H-pyrrolo[1,2-c]thiazole-7-carbonitrile is prepared as in Example 3.

APPLICATION EXAMPLE 16

A suspension of powdered potassium hydroxide (12.3 g) and a mixture (in the ratio 20/80) of 6-cyano- and 7-cyano-3-phenyl-5-(pyridin-3-yl)-1H,3H-pyrrolo[1,2-c]thiazole (11.3 g) in tert.-butyl alcohol (260 cc) is heated under reflux for 3 hours. The suspension is stirred for 16 hours at a temperature of the order of 20° C. and is then concentrated to dryness under reduced pressure (20 mm Hg; 2.7 kPa) at a temperature of the order of 60° C. The residue obtained is suspended in distilled water (300 cc) and is extracted 3 times with ethyl acetate (750 cc in total). The organic extracts are combined, washed 3 times with distilled water (300 cc in total), dried over anhydrous magnesium sulphate, treated with decolourising charcoal (0.5 g) and filtered, and the filtrate is concentrated to dryness under reduced pressure (20 mm Hg; 2.7 kPa) at a temperature of the order of 60° C. This gives a crude product (9.2 g). This product is chromatographed on a column of diameter 6 cm, containing silica (0.04–0.063 mm) (480 g). Elution is carried out with a mixture of ethyl acetate and methanol (95/5 by volume) under a pressure of 0.5 bar (51 kPa), 200 cc fractions being collected. The first 10 fractions are discarded. The next 12 fractions are combined and concentrated to dryness under reduced pressure (20 mm Hg; 2.7 kPa) at a temperature of the order of 60° C. This gives a product (7 g). This product is dissolved in ethanol (140 cc). The solution obtained is treated with a 2N ethanolic solution of hydrogen chloride (3.1 cc) and stirred at a temperature of the order of 20° C. for 15 minutes. The crystals which have appeared are filtered off, washed twice with ethanol (50 cc in total) and 3 times with diethyl ether (75 cc in total) and dried under reduced pressure (20 mm Hg; 2.7 kPa) at a temperature of the order of 20° C., in the presence of potassium hydroxide pellets. This gives 3-phenyl-5-(pyridin-3-yl)-1H, 3H-pyrrolo[1,2-c]thiazole-7-carboxamide hydrochloride (6 g) in the form of yellow crystals melting at 250° C.

The mixture (20/80) of 6-cyano and 7-cyano-3-phenyl-5-(pyridin-3-yl)-1H,3H-pyrrolo[1,2-c]thiazole can be prepared as described in Example 7.

APPLICATION EXAMPLE 17

A suspension of powdered potassium hydroxide (20.4 g) and a mixture (in the ratio 50/50) of 6-cyano and 7-cyano-3-methyl-5-(pyridin-3-yl)-1H,3H-pyrrolo[1,2-c]thiazole (17.6 g) in tert.-butyl alcohol (200 cc) is heated under reflux for 1 hour 20 minutes. The solvent is evaporated off under reduced pressure (20 mm Hg; 2.7 kPa) at a temperature of the order of 50° C. The residue is treated with a mixture of distilled water (200 cc) and methylene chloride (100 cc). The organic phase is separated off by decantation and the aqueous phase is extracted 4 times with methylene chloride (400 cc in total). The organic extracts are combined, washed 5 times with distilled water (750 cc in total), dried over anhydrous magnesium sulphate and filtered, and the filtrate is concentrated to dryness under reduced pressure (20 mm Hg; 2.7 kPa) at a temperature of the order of 50° C. This gives a product (19 g). This product is dissolved in methylene chloride (50 cc). Crystals appear; they are filtered off, washed 3 times with methylene chloride (15 cc in total) and dried under reduced pressure (20 mm Hg; 2.7 kPa), in the presence of potassium hydroxide pellets. This gives a product (6.1 g) melting at 170° C. The filtrate is chromatographed on a column of diameter 6 cm, containing silica (0.04-0.063 mm) (480 g). Elution is carried out with mixtures of ethyl acetate and methanol under a pressure of 0.5 bar (51 kPa), 250 cc fractions being collected. The first 13 fractions from elution with a mixture of ethyl acetate and methanol (97.5/2.5 by volume) are discarded. The next 3 fractions from elution with a mixture of ethyl acetate and methanol (95/5 by volume) and the next three fractions from elution with a mixture of ethyl acetate and methanol (95/5 by volume) are combined and concentrated to dryness under reduced pressure (20 mm Hg; 2.7 kPa) at a temperature of the order of 50° C. This gives a product (3.1 g), which is combined with the previously obtained product (6.1 g) and dissolved in boiling isopropanol (90 cc). The solution obtained is treated with decolourising charcoal (0.5 g) and filtered hot. The filtrate is cooled at a temperature of the order of 4° C. for 1 hour. The crystals which have appeared are filtered off, washed 3 times with isopropanol cooled to a temperature of the order of 4° C. (6 cc in total) and 3 times with diethyl ether (30 cc in total) and dried under reduced pressure (20 mm Hg; 2.7 kPa) at a temperature of the order of 20° C., in the presence of potassium hydroxide pellets. This gives 3-methyl-5-(pyridin-3-yl)-1H, 3H-pyrrolo[1,2-c]thiazole-7-carboxamide (5.6 g) in the form of cream crystals melting at 170° C.

The mixture (50/50) of 6-cyano and 7-cyano-3-methyl-5-(pyridin-3-yl)-1H,3H-pyrrolo[1,2-c]thiazole can be obtained as described in Example 6.

APPLICATION EXAMPLE 18

Triethylamine (50.1 g) is added in the course of 15 minutes, at a temperature of the order of 10° C., to a suspension of 2-aminoethanethiol hydrochloride (51.1 g) in ethanol (250 cc). The suspension obtained is stirred at a temperature of the order of 10° C. for 15 minutes and then filtered. The filtrate is treated with 5-(pyridin-3-yl)-1H,3H-pyrrolo[1,2-c]thiazole-7-carbonitrile (20.5 g) and the suspension obtained is heated at the boil for 22 hours. The solution obtained is cooled to a temperature of the order of 4° C. and the crystals which have appeared are filtered off, washed 3 times with ethanol cooled to a temperature of the order of 4° C. (75 cc in total) and 4 times with diethyl ether (100 cc in total) and then dried under reduced pressure (20 mm Hg; 2.7 kPa) at a temperature of the order of 20° C., in the presence of potassium hydroxide pellets. This gives a product (25 g) melting at 136° C. This product is combined with the product originating from another earlier operation (1.5 g) and dissolved in boiling ethanol (400 cc). The solution obtained is treated with decolourising charcoal (0.5 g) and filtered hot. The filtrate is cooled at a temperature of the order of 4° C. for 1 hour. The crystals which have appeared are filtered off, washed 3 times with ethanol (75 cc in total) and 3 times with diethyl ether (150 cc in total) and dried under reduced pressure (20 mm Hg; 2.7 kPa) at a temperature of the order of 20° C., in the presence of potassium hydroxide pellets. This gives a product (23 g) melting at 124° C. This product is dissolved in boiling acetonitrile (300 cc). The solution obtained is treated with decolourising charcoal (0.5 g) and filtered hot. The filtrate is cooled at a temperature of the order of 4° C. for 1 hour. The crystals which have appeared are filtered off, washed 3 times with acetonitrile cooled to a temperature of the order of 4° C. (75 cc in total) and 3 times with diethyl ether (150 cc in total) and then dried under reduced pressure (20 mm Hg; 2.7 kPa) at a temperature of the order of 20° C., in the presence of potassium hydroxide pellets. This gives 7-(4,5-dihydrothiazol-2-yl)-5-(pyridin-3-yl)-1H,3H-pyrrolo[1,2-c]thiazole (20.1 g) in the form of orange-yellow crystals melting at 124° C.

The 5-(pyridin-3-yl)-1H,3H-pyrrolo[1,2-c]thiazole-7-carbonitrile is prepared as in Example 3.

APPLICATION EXAMPLE 19

A suspension of 3-(pyridin-3-yl)-5,6,7,8-tetrahydroindolizine-1-carbonitrile (5.2 g) and powdered potassium hydroxide (7.7 g) in tert.-butyl alcohol (120 cc) is heated for 13 hours at a temperature of the order of 80° C. The suspension is then concentrated to dryness under reduced pressure (20 mm Hg; 2.7 kPa) at a temperature of the order of 60° C. The residue is taken up in distilled water (200 cc) and the suspension obtained is stirred at a temperature of the order of 20° C. for 1 hour. The crystals which have appeared are filtered off, washed 5 times with distilled water (250 cc in total) and dried under reduced pressure (20 mm Hg; 2.7 kPa) at a temperature of the order of 20° C., in the presence of potassium hydroxide pellets. This gives a crude product (4.1 g) melting at 180° C. This product, combined with the product prepared in the same way in another operation (1.1 g), is dissolved in boiling acetonitrile (160 cc). The turbid solution obtained is treated with decolourising charcoal (0.5 g) and filtered hot. The filtrate is cooled at a temperature of the order of 4° C. for 2 hours. The crystals which have appeared are filtered off, washed 3 times with acetonitrile (75 cc in total) and 3 times with isopropyl ether (75 cc in total) and then dried under reduced pressure (20 mm Hg; 2.7 kPa) at a temperature of the order of 20° C., in the presence of potassium hydroxide pellets. This gives 3-(pyridin-3-yl)-5,6,7,8-tetrahydroindolizine-1-carboxamide (4 g) in the form of light beige crystals melting at 184° C.

The 3-(pyridin-3-yl)-5,6,7,8-tetrahydroindolizine-1-carbonitrile can be prepared as in Example 8.

In human therapy, the products of the general formula (XIII) defined as above under A are particularly useful in the treatment of allergic and inflammatory complaints and, in general, of all complaints in which the physiopathological role of P.A.F.- acether can be incriminated. The doses depend on the desired effect and the duration of the treatment; for an adult, they are generally between 25 and 100 mg per day, administered orally, intravenously or by inhalation, in one or more individual doses.

In human therapy, the products of the general formula (XIII) defined as above under B are particularly useful in the prophylactic and therapeutic treatment of tnrombotic complaints. The doses depend on the desired effect and the duration of the treatment; for an adult, they are generally between 100 and 1,000 mg per day, administered orally in one or more individual doses, and between 10 and 100 mg, administered parenterally in one or more injections.

In general, the physician will determine the posology which he considers to be most appropriate to the age, the weight and all the other factors peculiar to the subject to be treated.

We claim:

1. A pyrrole derivative of the formula:

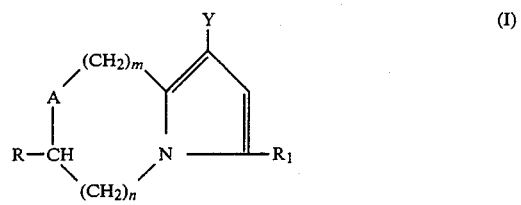

in which (a) Y represents a carboxyl radical or a radical of the formula:

in which $R_2$ represents an alkyl or benzyl radical, A represents a sulphur atom, m represents 1, n represents zero, R represent pyridin-3-yl and $R_1$ represents hydrogen; or (b) Y represents cyano, carboxyl, or a radical of the formula (II) as defined above, A represents sulphur, oxygen, or methylene, m represents 1 or 2 and n represents 0, 1 or 2, the sum of m+n being 1, 2 or 3, R represents hydrogen, alkyl, or phenyl, unsubstituted or substituted by halogen, alkyl, alkoxy or trifluoromethyl, and $R_1$ represents a radical of the formula:

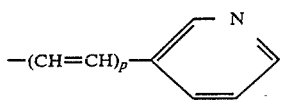  (III)

in which p represents zero or 1, the said alkyl radicals or alkyl radicals or alkyl portions being straight-chain or branched-chain and containing 1 to 4 carbon atoms each and its addition salts with acids and, where they exist, its metal salts and its addition salts with nitrogen bases.

2. A pyrrole derivative according to claim 1 wherein (a) Y represents —COOH or

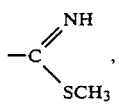

A represents sulphur, m is 1, n is 0, R is pyridin-3-yl, and $R_1$ is hydrogen, or (b) Y represents —CN, —COOH or

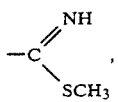

A represents sulfur or methylene, m is 1 or 2, n is 0 or 1, the sum of m+n being 1 or 2, R is hydrogen, methyl or phenyl, and $R_1$ is a radical of the formula:

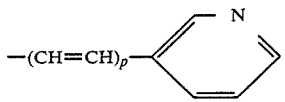

in which p is 0 or 1, and its addition salts with acids and, where they exist, its metal salts and its addition salts with nitrogen bases.

3. A compound according to claim 1 which is 3-(pyridin-3-yl)-1H,3H-pyrrolo[1,2-c]thiazole-7-carboxylic acid.

4. A compound according to claim 1 which is s-methyl 3-(pyridin-3-yl)-1H,3H-pyrrolo[1,2-c]thiazole-7-thiocarboximidate hydroiodide.

5. A compound according to claim 1 which is 5-(pyridin-3-yl)-1H,3H-pyrrolo[1,2-c]thiazole-7-carbonitrile.

6. A compound according to claim 1 which is 5-(pyridin-3-yl)-2,3-dihydro-1H-pyrrolizine-7-carbonitrile.

7. A compound according to claim 1 which is 6-cyano and 7-cyano-5-[2-(pyridin-3-yl)-vinyl]-1H,3H-pyrrolo[1,2-c]thiazole.

8. A compound according to claim 1 which is 6-cyano and 7-cyano-3-methyl-5-(pyridin-3-yl)-1H,3H-pyrrolo-[1,2-c]thiazole.

9. A compound according to claim 1 which is 6-cyano and 7-cyano-3-phenyl-5-(pyridin-3-yl)-1H,3H-pyrrolo[1, 2 -c]thiazole.

10. A compound according to claim 1 which is 3-(pyridin-3-yl)-5,6,7,8-tetrahydroindolizine-1-carbonitrile.

11. A compound according to claim 1 which is 6-(pyridin-3-yl)-3,4-dihydro-1H-pyrrolo[2,1-c]-1,4-thiazine-8-carbonitrile.

12. A compound according to claim 1 which is 6-(pyridin-3-yl)-1,2-dihydro-4H-pyrrolo[1,2-c]-1,3-thiazine-8-carbonitrile.

13. A compound according to claim 1 which is 5-(pyridin-3-yl-1H,3H-pyrrolo[1,2-c]thiazole-7-carboxylic acid.

14. A compound according to claim 1 which is S methyl 5-(pyridin-3-yl)-1H,3H-pyrrolo[1,2-c]thiazole-7-thiocarboximidate hydroiodide.

* * * * *